US006762045B2

(12) United States Patent
Krebs et al.

(10) Patent No.: US 6,762,045 B2
(45) Date of Patent: Jul. 13, 2004

(54) MEMBRANE DERIVED CASPASE-3, COMPOSITIONS COMPRISING THE SAME AND METHODS OF USE THEREFOR

(75) Inventors: Joseph F. Krebs, San Diego, CA (US); Anupama Srinivasan, Carlsbad, CA (US); Lawrence C. Fritz, Rancho Santa Fe, CA (US); Joe C. Wu, San Diego, CA (US)

(73) Assignee: Idun Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 10/103,448

(22) Filed: Mar. 20, 2002

(65) Prior Publication Data

US 2002/0155579 A1 Oct. 24, 2002

Related U.S. Application Data

(62) Division of application No. 09/718,234, filed on Nov. 20, 2000.

(51) Int. Cl.$^7$ .............................. C12N 9/64; C12N 5/00; C07H 21/04
(52) U.S. Cl. ..................... 435/226; 435/183; 435/219; 435/212; 435/252.3; 435/320.1; 435/325; 435/410; 435/6; 435/348; 435/254.2; 536/23.1; 536/23.2; 536/23.5
(58) Field of Search .............................. 435/348, 254.2, 435/183, 226, 219, 212, 252.3, 320.1, 325, 410; 536/231, 232, 235

(56) References Cited

U.S. PATENT DOCUMENTS 6,379,950 B1 * 4/2002 Alnemri .................. 435/320.1

OTHER PUBLICATIONS

Database Accession No. HS13737, Nov. 2, 1994.
Ahmad, M. et al., "Identification and Characterization of Murine Caspase–14, a New Member of the Caspase Family," *Cancer Research*, vol. 58, pp. 5201–5205, Nov. 15, 1998.
Lee, D. et al., "Potent and Selective Nonpeptide Inhibitors of Caspases 3 and 7 Inhibit Apoptosis and Maintain Cell Functionality," *Journal of Biol. Chem.*, 275(21):16007–16014, May 26, 2000.
Wei, Y. et al., "The Structures of Caspases–1, –3, –7 and –8 Reveal the Basis for Substrate and Inhibitor Selectivity," *Chemistry and Biology*, 7(6):423–432, May 30, 2000.
Virkajärvi, N. et al., "Apoptotic Index and Apoptosis Influencing Proteins bcl–2, mcl–1, bax and caspases 3, 6 and 8 in Pancreatic Carcinoma," *Histopathology*, 33(5):432–439, Nov. 1998.

Chandler et al., "Different Subcellular Distribution of Caspase–3 and Caspase–7 following Fas–induced Apoptosis in Mouse Liver," *The Journal of Biological Chemistry* 273(18): 10815–10818, May 1, 1998.
Cohen, Gerald M., "Caspases: the executioners of apoptosis," *Biochemical Journal* 326: 1–16, 1997.
Enari, et al., "A caspase–activated DNase that degrades DNA during apoptosis, and its inhibitor ICAD," *Nature 391*: 43–50, 1998.
Faleiro et al., "Multiple species of CPP32 and Mch2 are the major active caspases present in apoptotic cells," *EMBO 16*: 2271–2281, 1997.
Fernandes–Alnemri et al., "In vitro activation of CPP32 and Mch3 by Mch4, a novel human apoptotic cysteine protease containing two FADD–like domains," *Proceedings of the National Academy of Science USA 93*: 7464–7469, Jul. 1996.
Fernandes–Alnemri et al., "CPP32, a Novel Human Apoptotic Protein with Homology to *Caenoradbitis elegans* Cell Death Protein Ced–3 and Mammalian Interleukin– 1β–converting Enzyme," *Journal of Biological Chemistry 269*(49): 30761–30764, Dec. 9, 1994.
Fernandes–Alnemri et al., SwisProt 39 Database, Accession No. P42574, Nov. 1995.
Genbank Accession No. U13737, Apr. 14, 1995.
Kluck et al., "The Release of Cytochrome c from Mitochondria: A Primary Site for Bcl–2 Regulation of Apoptosis," *Science 275*: 1132–1136, Feb. 21, 1997.
Krajewska et al., "Immunohistochemical Analysis of in Vivo Patterns of Expression of CPP32 (Caspase–3), a Cell Death Protease," *Cancer Research 57*: 1605–1613, Apr. 15, 1997.
Krebs et al, "Activation of Membrane–associated Procaspase–3 Is Regulated by Bcl–2," *Journal of Cell Biology 144*(5): 915–926, Mar. 8, 1999.
Krebs et al., "Heavy membrane–associated caspase 3: identification, isolation, and characterization," *Biochemistry 39*(51):16056–16063, Dec. 26, 2000.
Li et al., "Cytochrome c and dATP–Dependent Formation of Apaf–1/Caspase–9 Complex Initiates an Apoptotic Protease Cascade," *Cell 91*: 479–489, Nov. 14, 1997.

(List continued on next page.)

*Primary Examiner*—Richard Hutson
(74) *Attorney, Agent, or Firm*—Seed Intellectual Property Law Group PLLC

(57) ABSTRACT

Provided are isolated nucleic acids encoding a novel membrane derived caspase-3 and polypeptides expressed therefrom. In one embodiment, the nucleic acid expression vectors that produce membrane derived caspase-3 polypeptide may be introduced into host cells as a gene delivery vehicle. In other embodiments, methods are provided for treating pathological disorders caused by altered apoptosis, such as autoimmune disease, cancer, viral infections, and bacterial infections. Another aspect of the invention is the use of the isolated nucleic acid encoding membrane derived caspase-3 and polypeptides expressed therefrom as a means for promoting or inhibiting programmed cell death.

21 Claims, 16 Drawing Sheets

OTHER PUBLICATIONS

Liu et al., "Induction of Apoptotic Program in Cell–Free Extracts: Requirement for dATP and Cytochrome c," *Cell 86*: 147–157, Jul. 12, 1996.

Liu et al., "DFF, a Heterodimeric Protein That Functions Downstream of Caspase–3 to Trigger DNA Fragmentation during Apoptosis," *Cell 86*: 175–184, Apr. 18, 1997.

Mancini et al., "The Caspase–3 Precursor Has a Cytosolic and Mitochondrial Distribution: Implications for Apoptotic Signaling," *Journal of Cell Biology 140*(6): 1485–1495, Mar. 23, 1998.

Martins et al., "Activation of Multiple Interleukin–1β Converting Enzyme Homologues in Cytosol and Nuclei of HL–60 Cells during Etoposide–induced Apoptosis," *The Journal of Biological Chemistry 272*(11): 7421–7430, Mar. 14, 1997.

Nicholson et al., "Identification and inhibition of the ICE/CED–3 protease necessary for mammalian apoptosis," *Nature 376*: 37–43, Jul. 6, 1995.

Orth et al., "Molecular Ordering of Apoptotic Mammalian CED–3/ICE–like Proteases," *The Journal of Biological Chemistry 271*(35): 20977–20980, Aug. 30, 1996.

Posmantur et al., "Characterization of CPP32–like Protease Activity Following Apoptotic Challenge in SH–SY5Y Neuroblastoma Cells," *Journal of Neurochemistry 68*(6): 2328–2337, 1997.

Quan et al., "Proteolytic activation of the cell death protease Yama/CPP32 by granzyme B," *Proceedings of the National Academy of Science USA 93*: 1972–1976, Mar. 1996.

Schlegel et al., "CPP32/Apopain Is a Key Interleukin 1β Converting Enzyme–like Protease Involved in Fas–mediated Apoptosis," *The Journal of Biological Chemistry 271*(4): 1841–1844, Jan. 26, 1996.

Stennicke et al., "Pro–caspase–3 Is a Major Physiologic Target of Caspase–8," *Journal of Biological Chemistry 273*(42): 27084–27090, Oct. 16, 1998.

Srinivasan et al., "In situ immunodetection of activated caspase–3 in apoptotic neurons in the developing nervous system," *Cell Death and Differentation 5*: 1004–1016, 1998.

Tewari et al., "Yama/CPP32β, a Mammalian Homolog of CED–3, Is a CrmA–Inhibitable Protease That Cleaves the Death Substrate Poly(ADP–Ribose) Polymerase," *Cell 81*: 801–809, Jun. 2, 1995.

Yang et al., "Prevention of Apoptosis by Bcl–2: Release of Cytochrome c from Mitochondria Blocked," *Science 275*: 1129–1132, Feb. 21, 1997.

* cited by examiner

| | |
|---|---|
| atg gag aac act gaa aac tca gtg gat tca aaa tcc att aaa aat ttg<br>Met Glu Asn Thr Glu Asn Ser Val Asp Ser Lys Ser Ile Lys Asn Leu<br>1                          5                     10                  15 | 48 |
| gaa cca aag atc ata cat gga agc gaa tca atg gac tct gga ata tcc<br>Glu Pro Lys Ile Ile His Gly Ser Glu Ser Met Asp Ser Gly Ile Ser<br>                     20                    25                   30 | 96 |
| ctg gac aac agt tat aaa atg gat tat cct gag atg ggt tta tgt ata<br>Leu Asp Asn Ser Tyr Lys Met Asp Tyr Pro Glu Met Gly Leu Cys Ile<br>              35                    40                   45 | 144 |
| ata att aat aat aag aat ttt cat aaa agc act gga atg aca tct cgg<br>Ile Ile Asn Asn Lys Asn Phe His Lys Ser Thr Gly Met Thr Ser Arg<br>    50                    55                    60 | 192 |
| tct ggt aca gat gtc gat gca gca aac ctc agg gaa aca ttc aga aac<br>Ser Gly Thr Asp Val Asp Ala Ala Asn Leu Arg Glu Thr Phe Arg Asn<br>65                        70                    75                80 | 240 |
| ttg aaa tat gaa gtc agg aat aaa aat gat ctt aca cgt gaa gaa att<br>Leu Lys Tyr Glu Val Arg Asn Lys Asn Asp Leu Thr Arg Glu Glu Ile<br>                     85                    90                   95 | 288 |
| gtg gaa ttg atg cgt gat gtt tct aaa gaa gat cac agc aaa agg agc<br>Val Glu Leu Met Arg Asp Val Ser Lys Glu Asp His Ser Lys Arg Ser<br>                   100                 105                110 | 336 |
| agt ttt gtt tgt gtg ctt ctg agc cat ggt gaa gaa gga ata att ttt<br>Ser Phe Val Cys Val Leu Leu Ser His Gly Glu Glu Gly Ile Ile Phe<br>         115                    120                 125 | 384 |
| gga aca aat gga cct gtt gac ctg aaa aaa ata aca aac ttt ttc aga<br>Gly Thr Asn Gly Pro Val Asp Leu Lys Lys Ile Thr Asn Phe Phe Arg<br>    130                    135                140 | 432 |
| ggg gat cgt tgt aga agt cta act gga aaa ccc aaa ctt ttc att att<br>Gly Asp Arg Cys Arg Ser Leu Thr Gly Lys Pro Lys Leu Phe Ile Ile<br>145                       150                 155                160 | 480 |
| cag gcc tgc cgt ggt aca gaa ctg gac tgt ggc att gag aca gac agt<br>Gln Ala Cys Arg Gly Thr Glu Leu Asp Cys Gly Ile Glu Thr Asp Ser<br>                   165                 170                175 | 528 |
| ggt gtt gat gat gac atg gcg tgt cat aaa ata cca gtg gat gcc gac<br>Gly Val Asp Asp Asp Met Ala Cys His Lys Ile Pro Val Asp Ala Asp<br>             180                    185                190 | 576 |
| ttc ttg tat gca tac tcc aca gca cct ggt tat tat tct tgg cga aat<br>Phe Leu Tyr Ala Tyr Ser Thr Ala Pro Gly Tyr Tyr Ser Trp Arg Asn<br>         195                    200                 205 | 624 |
| tca aag gat ggc tcc tgg ttc atc cag tcg ctt tgt gcc atg ctg aaa<br>Ser Lys Asp Gly Ser Trp Phe Ile Gln Ser Leu Cys Ala Met Leu Lys<br>    210                    215                 220 | 672 |
| cag tat gcc gac aag ctt gaa ttt atg cac att ctt acc cgg gtt aac<br>Gln Tyr Ala Asp Lys Leu Glu Phe Met His Ile Leu Thr Arg Val Asn<br>225                       230                 235                240 | 720 |
| cga aag gtg gca aca gaa ttt gag tcc ttt tcc ttt gac gct act ttt<br>Arg Lys Val Ala Thr Glu Phe Glu Ser Phe Ser Phe Asp Ala Thr Phe<br>                   245                 250                255 | 768 |
| cat gca aag aaa cag att cca tgt att gtt tcc atg ctc aca aaa gaa<br>His Ala Lys Lys Gln Ile Pro Cys Ile Val Ser Met Leu Thr Lys Glu<br>             260                    265                270 | 816 |
| ctc tat ttt tat cac taa<br>Leu Tyr Phe Tyr His *<br>         275 | 834 |

Residue:
1          10          20          30
           ↓                       ↓
MENTENSVDSKSIKNLEPKIIHGSESMDSG

A.

B.

MEMBRANE DERIVED CASPASE-3, COMPOSITIONS COMPRISING THE SAME AND METHODS OF USE THEREFOR

CROSS-REFERENCE TO RELATED APPLICATION

This application is a divisional of U.S. patent application Ser. No. 09/718,234, filed Nov. 20, 2000, now pending, which application is incorporated herein by reference in its entirety.

TECHNICAL FIELD

The present invention relates generally to caspases and their role in apoptosis, and in particular, to nucleic acids encoding membrane derived caspase-3, the encoded polypeptides, antibodies thereto, and methods of producing and using membrane derived caspase-3 polypeptide.

BACKGROUND OF THE INVENTION

The normal physiological process of programmed cell death, also known as apoptosis, plays a critical role in the maintenance of tissue homeostasis. The apoptotic process in multicellular organisms ensures that the rate of new cell accumulation produced by cell division is offset by a commensurate rate of cell loss due to death. A typical result of apoptosis are certain morphological changes in a cell, including fragmentation of nuclear chromatin, compaction of cytoplasmic organelles, dilatation of the endoplasmic reticulum, decreased cell volume, and alterations in the plasma membrane. The end result of programmed cell death is phagocytosis of apoptotic cells and prevention of an inflammatory response. Disturbances in apoptosis that prevent or delay normal cell turnover can be just as important to the pathogenesis of diseases as are known abnormalities in the regulation of cell proliferation and the cell cycle. Similar to cell division, which is controlled by complex interactions between cell cycle regulatory proteins, apoptosis is regulated under normal circumstances by a complex network of gene products that interact to either induce or inhibit cell death.

The stimuli that regulate the function of these apoptotic gene products include both extracellular and intracellular signals. Either the presence or removal of a particular stimulus can be sufficient to evoke a positive or negative apoptotic signal. Physiological stimuli that inhibit or reduce the likelihood of apoptosis include, for example, growth factors, extracellular matrix, CD40 ligand, viral gene products, neutral amino acids, zinc, estrogen, and androgens. In contrast, stimuli that promote apoptosis include, for example, tumor necrosis factor (TNF), Fas, transforming growth factor β (TGF$^β$), neurotransmitters, growth factor withdrawal, loss of extracellular matrix attachment, intracellular calcium, and glucocorticoids. Other stimuli, including those of environmental and pathogenic origin, may also induce or inhibit apoptosis. Although diverse signals and complex interactions of cellular gene products mediate apoptosis, the results of these interactions ultimately lead into a cell death pathway that is evolutionarily conserved between humans and invertebrates.

Several gene families and products that modulate the apoptotic process have now been identified. One family is the Bcl-2 proteins, which can function to modulate apoptosis in a wide variety of cell systems (Oltvai and Korsmeyer, Cell 79:189–192, 1994; Reed, Nature 387:773–776, 1997). The over-expression of Bcl-2 has been shown to inhibit the activation of cytoplasmic caspases following apoptotic stimuli in several cell systems (Armstrong et al., J. Biol. Chem. 271:16850–16855, 1996; Chinnaiyan et al., J. Biol. Chem. 271:4573–4576, 1996; Boulakia et al., Oncogene 12:29–36, 1996; Srinivasan et al., J. Neurosci. 16:5654–60, 1996). Although Bcl-2 inhibits the onset of apoptosis, it does not impede already initiated apoptosis (McCarthy et al., J. Cell Biol. 136:215–217, 1997). Most Bcl-2 family members associate with cellular membranes, such as the mitochondrial outer membrane, the nuclear envelope, and the endoplasmic reticulum (Reed, Nature 387:773–776, 1997; Krajewski et al., Cancer Res. 53:47014714, 1993; Yang et al., J. Cell. Biol. 128:1173–1184, 1995; Lithgow et al., Cell Growth Differ. 3:411–417, 1994); however, it remains unclear how the membrane bound Bcl-2 exerts control over another key set of apoptosis regulators, the soluble cytoplasmic, aspartate-specific cysteine proteases ("caspases").

The caspase family of cysteine proteases are essential effectors of the apoptotic process (Yuan et al., Cell 75:641–652, 1993; Alnemri et al., Cell 87:171, 1996; Cohen, Biochem. 326:1–16, 1997; Miller, Semin. Immunol 9:35–49, 1997; Salvesen and Dixit, Cell 91:443–446, 1997). Caspases are synthesized as inactive zymogens, which are activated by proteolytic processing to yield large (~18 kDa) and small (~12 kDa) subunits that associate to form active enzymes (Thornberry et al., Nature 396:768–774, 1992; Nicholson et al., Nature 376:37–43, 1995; Stennicke and Salvesen, J. Biol. Chem. 272:25719–25723, 1997). Diverse apoptotic stimuli cause the activation of specific caspases which then initiate a protease cascade by proteolytically processing additional caspases (Srinivasula et al., Proc. Natl. Acad Sci USA 93:14486–14491, 1996; Yu et al., Cancer Res. 58:402–408, 1998). Once activated, these downstream (executioner) caspases kill cells by cleaving specific molecular targets that are essential for cell viability or by activating additional pro-apoptotic factors (Liu et al., Cell 89:175–184, 1997; Enari et al., Nature 391:43–50, 1998; Salvesen and Dixit, Cell 91:443446, 1997).

Caspase-3 is an example of a downstream "executioner" caspase thought to cleave a number of important cellular proteins involved in DNA replication, DNA repair, RNA splicing, protein phosphorylation, and chromosomal fragmentation during apoptosis (Cohen et al., Biochem. J. 326:1–16, 1997, Enari et al., Nature 391:43–50, 1998, Liu et al., Cell 89:175–84, 1997). This enzyme is synthesized as a 32 kDa procaspase that is processed into mature 20/17 kDa (large) and 12 kDa (small) subunits by cleavage at Asp 9, Asp 28, and Asp 175 (Fernandes-Alnemri et al., J. Biol. Chem. 269:30761–64, 1994; Tewari et al., Cell, 81:801–9, 1995; Fernandes-Alnemri et al., Proc.Natl.Acad.Sci. USA, 93:7464–69, 1996, Nicholson et al., Nature 376:37–43, 1995). Procaspase-3 can be activated by a number of proteases involved in apoptosis, including caspases-1, -8, -9, and -10, as well as the serine protease Granzyme B (Stennicke et al., J. Biol. Chem. 273:27084–90, 1998, Fernandes-Alnemri et al., Proc.Natl.Acad.Sci. USA, 93:7464–69, 1996; Quan et al., Proc Natl Acad Sci USA, 93:1972–76, 1996, Krebs et al., J. Cell Biol. 144:915–26, 1999). Immunocytochemical experiments indicate that procaspase-3 is primarily a cytoplasmic protein (Krajewski et al., Cancer Res. 57:1605–13, 1997; Posmantur et al., J. Neurochem. 68:2328–37, 1997; Chandler et al., J. Biol. Chem. 273:10815–18, 1998), while activated caspase-3-like enzyme is found in the cytoplasm and the nucleus (Martins et al., J. Biol. Chem. 272:7421–30, 1997). Additionally, it was reported that procaspase-3 may localize to the mitochondrial intermembrane space (Mancini et al., *J. Cell Biol.* 140:1485–95, 1998).

The dysfunction or loss of regulated apoptosis can lead to a variety of pathological disease states because apoptosis maintains tissue homeostasis in a range of physiological processes, including embryonic development, immune cell regulation and normal cellular turnover. For example, the loss of apoptosis can lead to the accumulation of self-reactive lymphocytes associated with many autoimmune diseases. Additionally, abnormal loss or inhibition of apoptosis can also lead to the accumulation of virally infected cells and hyperproliferative cells, such as neoplastic or tumor cells. Similarly, the irregular activation of apoptosis can contribute to a variety of pathological disease states, including, for example, acquired immunodeficiency syndrome (AIDS), neurodegenerative diseases, and ischemic injury. Treatments that are specifically designed to modulate the apoptotic pathways in these and other pathological conditions can change the natural progression of many of these diseases.

Thus, there exists a need to identify apoptotic genes and their gene products and methods of modulating apoptosis for the therapeutic treatment of human diseases. The present invention satisfies this need and provides related advantages as well.

SUMMARY OF THE INVENTION

The present invention provides in part the discovery of a novel membrane derived caspase-3 polypeptide or functional fragment thereof and isolated nucleic acid molecules encoding such polypeptides. The present invention also provides membrane derived caspase-3 polypeptide encoding nucleic acid molecules in vectors, host cells, gene delivery vehicles, and kits, as well as antibodies directed to naturally and recombinantly expressed membrane derived caspase-3 polypeptide. The present invention also provides methods of inducing apoptosis, of treating certain diseases, and of identifying an agent that alters the activity of membrane derived caspase-3 polypeptide.

In one aspect, the present invention provides an isolated nucleic acid molecule consisting essentially of a sequence encoding membrane derived caspase-3 polypeptide of SEQ ID NO:3. In one embodiment, the nucleic acid molecule encodes membrane derived caspase-3 polypeptide of SEQ ID NO:3 that oligomerizes with a caspase. In another embodiment, the invention provides a vector having an isolated molecule consisting essentially of a sequence encoding membrane derived caspase-3 polypeptide of SEQ ID NO:3.

In another aspect, the present invention provides an isolated nucleic acid molecule encoding a membrane derived caspase-3 consisting essentially of a single stranded or double stranded polynucleotide sequence of SEQ ID NO:2. In another embodiment, the invention provides a vector having an isolated nucleic acid molecule encoding a membrane derived caspase-3 consisting essentially of a single stranded or double stranded polynucleotide sequence of SEQ ID NO:2.

In a related embodiment, the aforementioned vectors are a viral vector. In another embodiment, a nucleic acid expression vector having any one of the aforementioned nucleic acid molecules wherein the nucleic acid molecule is operably linked to a promoter. In a further embodiment, the invention provides the nucleic acid expression vector wherein the promoter is an inducible promoter. In yet another embodiment, the aforementioned nucleic acid expression vectors are individually contained in a host cell. In a further embodiment, the invention provides a host cell containing the aforementioned nucleic acid expression vectors wherein the host cell is selected from the group consisting of a bacterium, a yeast cell, a nematode cell, an insect cell, and a mammalian cell.

In another aspect, the invention provides an isolated membrane derived caspase-3 polypeptide consisting essentially of SEQ ID NO:3. In one embodiment, the invention provides the isolated membrane derived caspase-3 polypeptide consisting essentially of SEQ ID NO:3 wherein the polypeptide oligomerizes with a caspase. In another embodiment, the aforementioned polypeptide oligomerizes with a caspase wherein the caspase is selected from the group consisting of caspase-1, caspase-2, caspase-3, caspase-4, caspase-5, caspase-6, caspase-7, caspase-8, caspase-9, caspase-10, caspase-11, caspase-12, caspase-13, and caspase-14.

In another aspect, the invention provides an antibody specific for a membrane derived caspase-3 polypeptide, the polypeptide consisting essentially of SEQ ID NO:3. In one embodiment, the invention provides the aforementioned antibody wherein the antibody is a monoclonal antibody. In another embodiment, the invention provides a cell expressing any one of the aforementioned antibodies.

In another aspect, the invention provides an antibody that does not specifically recognize a cytoplasmic derived caspase-3 and does specifically recognize a membrane derived caspase-3 polypeptide, the membrane derived caspase-3 polypeptide consisting essentially of SEQ ID NO:3.

In another aspect, the invention provides an antibody that specifically recognizes a cytoplasmic derived caspase-3 and does not specifically recognize a membrane derived caspase-3 polypeptide, the membrane derived caspase-3 polypeptide consisting essentially of SEQ ID NO:3.

In another aspect, the invention provides a method of producing a membrane derived caspase-3 polypeptide, comprising culturing a host cell containing a nucleic acid expression vector comprising at least one promoter operaby linked to a nucleic acid molecule encoding a membrane derived caspase-3 polypeptide, the nucleic acid molecule consisting essentially of SEQ ID NO:2, under conditions and for a time sufficient for expression of the polypeptide. In one embodiment, the aforementioned method includes the nucleic acid expression vector having a promoter that is inducible. In a further embodiment, the invention provides the aforementioned methods further comprising the step of contacting the host cell with a caspase activator under conditions and for a time sufficient to activate the membrane derived caspase-3 polypeptide. In yet another embodiment, the invention provides the aforementioned methods further the host cell expressing a caspase activator under conditions and for a time sufficient to activate the membrane derived caspase-3 polypeptide. In still another embodiment, the activator of the aforementioned methods, wherein the activator is selected from the group consisting of caspase-1, caspase-8, caspase-9, caspase-10, and Granzyme B.

In another aspect, the invention provides a membrane derived caspase-3 polypeptide produced by any one of the aforementioned methods.

In another aspect, the invention provides a method of inducing apoptosis in a cell, comprising delivering to a cell an effective amount of an isolated nucleic acid molecule encoding a membrane derived caspase-3 polypeptide, the nucleic acid molecule consisting essentially of SEQ ID NO:2, under conditions and for a time sufficient for expression of the polypeptide and therefrom detecting apoptosis of the cell. In one embodiment, the aforementioned method of inducing apoptosis wherein the cell comprises a tissue culture cell. In a further embodiment, the aforementioned method of inducing apoptosis wherein the tissue culture cell is selected from the group consisting of 697 lymphoblastoid cells, E15 primary brain cortical cells, MN9D cells, Jurkat T cells, THP-1 cells, and FL5. 12 cells. In another embodiment, the aforementioned method of inducing apoptosis wherein the step of delivering to the cell is selected from the group consisting of injection, transfection, transformation, electroporation, and receptor mediated endocytosis. In yet another embodiment, the aforementioned method of inducing apoptosis wherein the step of delivering administering the nucleic acid molecule to the circulatory system of a warm-blooded mammal in which the cell is located. In still another embodiment, the aforementioned method of inducing apoptosis wherein step of apoptosis detection is selected from the group consisting of altered cellular morphology, DNA fragmentation, annexin binding, caspase activity, and mitochondrial release of cytochrome c.

In another aspect, the invention provides a method of inducing apoptosis in a cell, comprising delivering to a cell an effective amount of a membrane derived caspase-3 polypeptide, the polypeptide consisting essentially of SEQ ID NO:3, under conditions and for a time sufficient to detect therefrom the induction of apoptosis of the cell. In one embodiment, the aforementioned method of inducing apoptosis in a cell wherein the of delivering to the cell comprises injecting the polypeptide. In another embodiment, the aforementioned method of inducing apoptosis wherein step of apoptosis detection is selected from the group consisting of altered cellular morphology, DNA fragmentation, annexin binding, caspase activity, and mitochondrial release of cytochrome c.

In another aspect, the invention provides a gene delivery vehicle comprising any one of the aforementioned nucleic acid molecules wherein the nucleic acid molecule is operably linked to a promoter. In one embodiment, the aforementioned gene delivery vehicle wherein the vehicle is a retrovirus or adenovirus. In another embodiment, the aforementioned gene delivery vehicle wherein the acid molecule is associated with a polycation. In a further embodiment, the aforementioned gene delivery vehicle further comprising a ligand that binds a cell surface receptor.

In a related embodiment, the invention provides a method of treating cancer, comprising administering to a patient any one of the aforementioned gene delivery vehicles, wherein the gene delivery vehicle is internalized by tumor cells. In another embodiment, the invention provides a method of treating autoimmune disease, comprising administering to a patient any one of the aforementioned gene delivery vehicles, wherein the gene delivery vehicle is internalized by cells mediating autoimmune disease. In yet another embodiment, the invention provides a method of treating viral infections, comprising administering to a patient any one of the aforementioned gene delivery vehicles, wherein the gene delivery vehicle is internalized by virally-infected cells. In still another embodiment, the invention provides a method of treating bacterial infections, comprising administering to a patient any one of the aforementioned gene delivery vehicles, wherein the gene delivery vehicle is internalized by bacterially-infected cells.

In another aspect, the invention provides a kit for screening for agents that alter apoptosis, comprising a host cell and an isolated nucleic acid molecule consisting essentially of a sequence encoding a membrane derived caspase-3 polypeptide of SEQ ID NO:3. In one embodiment, the aforementioned kit wherein the host cell is a eukaryotic cell. In another embodiment, the aforementioned kit wherein the eukaryotic host cell is selected from the group consisting of 697 lymphoblastoid cells, E15 primary brain cortical cells, MN9D cells, Jurkat T cells, THP-1 cells, and FL5. 12 cells.

In another aspect, the invention provides a kit for screening for agents that alter apoptosis, comprising a membrane derived caspase-3 polypeptide, the polypeptide consisting essentially of SEQ ID NO:3 and a detection reagent that specifically binds to at least one of the foregoing polypeptides. In one embodiment, the aforementioned kit wherein the detection reagent is an antibody or antigen-binding fragment thereof.

In another aspect, the invention provides a composition, comprising a membrane derived caspase-3 polypeptide consisting essentially of SEQ ID NO:3, and an excipient or diluent.

In another aspect, the invention provides a method for identifying an agent that alters the activity of a membrane derived caspase-3 polypeptide consisting essentially of SEQ ID NO:3, comprising contacting the membrane derived caspase-3 polypeptide with a caspase substrate in the presence and absence of at least one candidate agent, and comparing the levels of caspase substrate turnover and therefrom identifying an agent that alters the activity of the membrane derived caspase-3 polypeptide. In one embodiment, the aforementioned method wherein the caspase substrate comprises a site cleaved by a caspase selected from the group consisting of a protein, a polypeptide, an oligopeptide, a peptide mimetic and a peptide. In another embodiment, the aforementioned methods wherein the substrate comprises the peptide DEVD. In a further embodiment, the aforementioned methods wherein the membrane derived caspase-3 polypeptide is part of a membrane fraction. In still another embodiment, the aforementioned methods wherein membrane fraction comprises membranes selected from the group consisting of heavy membranes and nuclear membranes. In yet another embodiment, the aforementioned methods wherein membrane fraction comprises a heavy membranes and nuclear membranes. In another embodiment, the aforementioned methods wherein substrate turnover is detected by time course analysis or endpoint analysis. In still another embodiment, the aforementioned methods wherein caspase substrate turnover detection is performed by a method selected from the group consisting of fluorescence spectroscopy, mass spectrometry, HPLC, colorimetry, fluorography, radiography, gel electrophoresis, chromatography and N-terminal peptide sequencing. In a further embodiment, the aforementioned methods further comprising incubating the membrane derived caspase-3 polypeptide with a caspase activator prior to or concurrent with the addition of the caspase substrate.

In another aspect, an agent identified by any one of the aforementioned methods that alters the activity of a membrane derived caspase-3 polypeptide consisting essentially of SEQ ID NO:3. In one embodiment, the aforementioned agent wherein the agent inhibits or enhances the activity of the membrane derived caspase-3 polypeptide.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1 is the nucleic acid sequence of human cytoplasmic procaspase-3 along with the corresponding amino acid translation (SEQ ID NO:1). The numbers on the right correspond to the nucleic acid sequence and the numbers between the lines of sequence correspond to the amino acids. The * designates the stop codon.

FIG. 2A illustrates the activation of DEVD-amc (SEQ ID NO:6) cleavage activity by caspase-1 and inhibition by YVADaldehyde (SEQ ID NO:7). FIG. 2B is a scanned image of an immunoblot representing membrane derived procaspase processing. The positions of the molecular weight markers (kDa) are indicated to the right. The arrows indicate the large subunits of the activated caspases.

FIG. 9A illustrates the spontaneous activation of caspase activity in heavy membrane from 697-neo and 697-Bcl-2 cells as a function of DEVD-amc turnover. FIG. 9B illustrates the generation of soluble caspase activity from membranes as a function of DEVD-amc turnover.

FIG. 12A illustrates the caspase activity present in the heavy membrane fraction. FIG. 12B illustrates the caspase activity present in the cytoplasmic fraction.

FIG. 13A is a graph demonstrating the effects of NP-40 on spontaneous and induced caspase activities in neo-membranes. FIG. 13B is a graph illustrating the effect of NP-40 on spontaneous caspase activation in Bcl-2 and neo-membranes. FIG. 13C is a graph depicting NP-40-dependent and independent activation of procaspase-3 by granzyme B treatment of mitochondrial enriched fractions.

DETAILED DESCRIPTION OF THE INVENTION

Figure 2A:
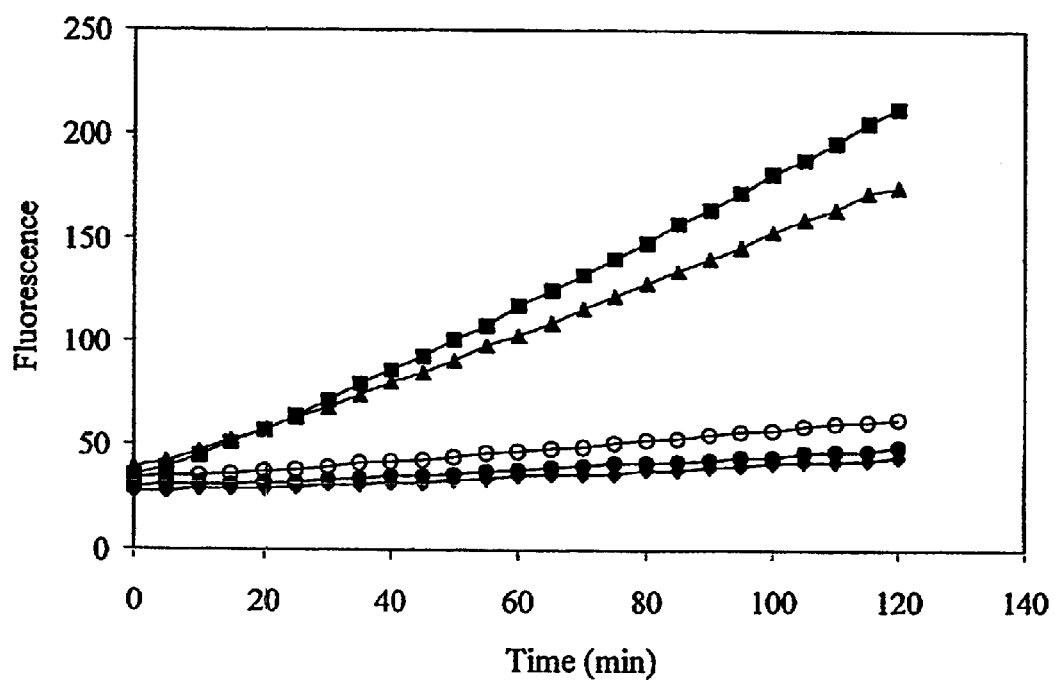
FIGS. 2A and 2B are graphs and immunoblots of activation by caspase-1 of membrane derived procaspase-3 from 697 cells.

As noted above, the present invention is generally directed to isolated nucleic acids encoding a novel membrane derived caspase-3 and to the polypeptides expressed therefrom. One application of the disclosed invention is to prepare nucleic acid expression vectors for preparing membrane derived caspase-3 polypeptide. In certain aspects, the nucleic acid expression vectors that produce membrane derived caspase-3 polypeptide may be introduced into host cells as a gene delivery vehicle. As provided herein, a preferred method utilizes a gene delivery vehicle to treat pathological disorders caused by altered apoptosis, such as autoimmune diseases, cancer, bacterial infections and viral infections. Another aspect of the subject invention is the use of the isolated nucleic acid encoding membrane derived caspase-3 and polypeptides expressed therefrom as a means for promoting or inhibiting programmed cell death at a critical initiation point (i.e., membranes). Accordingly, by using such nucleic acids and polypeptides, control points upstream of the cytoplasmic apoptotic pathway may be effectively assayed and treatment of disorders caused by aberrant apoptosis may be readily utilized.

A. Membrane Derived Caspase-3

The present invention is directed generally to membrane derived caspase-3 polypeptides, which as provided herein may include any membrane derived caspase-3 variant, and in addition methods for producing recombinant membrane derived caspase-3 polypeptides by culturing host cells containing nucleic acid expression vectors encoding membrane derived caspase-3. The invention is also directed to methods of inducing apoptosis by using isolated nucleic acid molecules encoding membrane derived caspase-3 polypeptide that have the nucleotide sequence of SEQ ID NO:2, or using isolated membrane derived caspase-3 polypeptides that have the deduced amino acid sequence of SEQ ID NO:3 (compare to full length nucleic acid and amino acid sequences of cytoplasmic procaspase-3 (SEQ ID NO:1) in FIG. 1). The polypeptides and nucleic acids of the present invention are preferably provided in an isolated form, and in certain preferred embodiments are purified to substantial homogeneity.

As used herein, "isolated" refers to material that has been separated from its original environment (e.g., the natural environment if it is naturally occurring). For example, a naturally occurring nucleic acid or polypeptide present in a living animal is not isolated, but the same nucleic acid or polypeptide is isolated when separated from some or all of the co-existing materials in the natural system. Nucleic acids or polypeptides may be part of a composition and still be isolated in that such fragment, vector, or composition is not part of its natural environment. Thus, an "isolated nucleic acid molecule" refers to a polynucleotide molecule in the form of a separate fragment or as a component of a larger nucleic acid construct, that has been separated from its source cell (including the chromosome it normally resides in) at least once in a substantially pure form. Nucleic acid molecules may be comprised of a wide variety of nucleotides, including DNA, RNA, nucleotide analogues, or some combination of these.

In a preferred embodiment, the present invention relates to an isolated membrane derived caspase-3 polypeptide consisting essentially of SEQ ID NO:3. In addition, the invention provides a functional fragment of SEQ ID NO:3 or splice variants thereof. A functional fragment of SEQ ID NO:3 is defined structurally and functionally in that it has the same contiguous sequence as a portion of SEQ ID NO:3 and at least one biological activity characteristic of membrane derived caspase-3. A functional fragment or a splice variant thereof preferably comprises at least 8, more preferably 9–15, even more preferably 16–49, and most preferably at least 50 contiguous residues of SEQ ID NO:3. A biological activity of a membrane derived caspase-3 polypeptide or functional fragment thereof of SEQ ID NO:3 is an activity of caspase-3 and can be, for example, the ability to bind a ligand, have protease or other enzymatic activity, enhance or inhibit apoptosis, or bind or induce the production of an anti-membrane derived caspase-3 antibody.

An isolated membrane derived caspase-3 polypeptide or functional fragment thereof may be obtained by a variety of methods known in the art. For example, a membrane derived caspase-3 polypeptide can be isolated by biochemical methods such as affinity chromatography. Affinity matrices that can be used for membrane derived caspase-3 polypeptide isolation can be a solid phase having attached thereto anti-membrane derived caspase-3 monoclonal, monospecific, or polyclonal antibodies prepared against a membrane derived caspase-3 polypeptide having a membrane derived caspase-3 epitope. Alternatively, ligands such as substrate analogues or enzymatic inhibitors of membrane derived caspase-3 may be used as affinity matrices to isolate a membrane derived caspase-3 polypeptide that binds the ligand.

Other biochemical methods for isolating a membrane derived caspase-3 polypeptide or functional fragment thereof include preparative gel electrophoresis, gel filtration, affinity chromatography, ion exchange and reversed phase chromatography, chromatofocusing, isoelectric focusing and sucrose or glycerol density gradients (Deutscher, *Methods in Enzymology: Guide to Protein Purification*, Vol. 182, Academic Press, Inc., San Diego (1990), Chapter 38; Balch et al., *Methods in Enzymology*, Vol. 257, Academic Press, Inc., San Diego (1995), Chapter 8). For example, a membrane derived caspase-3 polypeptide can be isolated by preparative polyacrylamide gel electrophoresis and elution by diffusion or electroelution (Deutscher, supra, 1990, Chapter 33). Continuous elution gel electrophoresis using a system such as the Model 491 Prep Cell (BioRad, Hercules, Calif.) can be used to isolate a membrane derived caspase-3 polypeptide. If desired, continuous elution gel electrophoresis may be combined with further purification steps such as liquid phase preparative isoelectric focusing using, for example, the Rotofor system (BioRad).

Also as used herein, "caspase" refers to a cysteine protease that specifically cleaves proteins after aspartate (Asp) residues. Caspases are initially expressed as zymogens (i.e., proenzymes or procaspases), in which a large subunit is N-terminal to a small subunit. Caspases are generally activated by cleavage at internal Asp residues and share a conserved pentapeptide sequence (QACRG; SEQ ID NO:5) within the active site. These proteins have been identified in many eukaryotes, including *C. elegans*, Drosophila, mouse, and human, and are typically soluble proteins. Currently, there are at least 14 known caspase genes, named caspase-1 through caspase-14. Table 1 recites ten human caspases along with their alternative names.

TABLE 1

| Caspase | Alternative name |
|---|---|
| Caspase-1 | ICE |
| Caspase-2 | ICH-1 |
| Caspase-3 | CPP32, Yama, apopain |
| Caspase-4 | $ICE_{rel}II$; TX, ICH-2 |
| Caspase-5 | $ICE_{rel}III$; TY |
| Caspase-6 | Mch2 |
| Caspase-7 | Mch3, ICE-LAP3, CMH-1 |
| Caspase-8 | FLICE; MACH; Mch5 |
| Caspase-9 | ICE-LAP6; Mch6 |
| Caspase-10 | Mch4, FLICE-2 |

The present invention relates generally to the surprising discovery that there exists an alternatively spliced form of caspase-3 derived from the membrane component of a cell. As used herein, "membrane derived caspase polypeptide" refers to polypeptides, including fragments and variants thereof as described herein, that may be associated with heavy or nuclear membranes on the inner or outer surface of such membranes (by direct interaction with the membrane or by interaction with other membrane protein(s)), that may be an integral polypeptide that is possibly exposed on one or both sides of a membrane, and that may be released from membranes. Without wishing to be bound by theory, membrane derived caspase-3 dissociates from the membranes once activated and this dissociation is not inhibited by the over-expression of Bcl-2, indicating that activated membrane derived caspase-3 does not appreciably bind to the Bcl-2 protein (or Bcl-2/caspase adapter molecules). In addition, membrane derived procaspase-3 is not catalytically active, which also suggests that membrane association itself does not inhibit activation. The mechanism of dissociation of the activated membrane derived caspase-3 from the membrane may be caused by a conformational change in the caspase polypeptide that disrupts a membrane complex or may be due to inactivation of protein(s) within a putative heavy membrane complex by caspase-mediated proteolysis.

As described herein, peptide sequencing data indicate that the activated (i.e., proteolytically cleaved) membrane derived caspase-3 polypeptide has an N-terminus that begins with Lys 14, whereas the cytoplasmic caspase-3 begins with Ser 10 or Ser 29. Without wishing to be bound by theory, the residues near the N-terminus of the protein may play an important regulatory role that controls the localization and specific activation of membrane derived caspase-3 polypeptide even though the alternative splicing has no detectable effect on catalytic activity or inhibitor binding of the polypeptide. Accordingly, utilizing membrane derived caspase-3 may aid in identifying a membrane protease that specifically activates caspase-3. Further, in view of the localization of Bcl-2 to heavy membranes, the localization of procaspase-3 to membranes may allow the suppression of procaspase activation, but as described herein, caspase-1 treatment is capable of overcoming the Bcl-2 suppression. Thus, the compositions and methods of the present invention will be useful for modulating apoptosis in the therapeutic treatment of human diseases.

Within the context of this invention, it should be understood that a caspase polypeptide, or a caspase polypeptide encoded by nucleic acid expression vectors, includes wild-type (i.e., native) protein sequences as well as other fragments, derivatives, analogs, or variants (including alleles) of the native protein sequence. Briefly, such fragments, derivatives, analogs, or variants, which are used interchangeably herein, may result from natural polymorphisms or may be engineered by recombinant methodology and retain essentially the same biological function or activity as the native polypeptide. Variants may differ from wild-type protein by one or more amino acid substitutions, insertions, deletions, or the like. Typically, when engineered, amino acid substitutions will be conservative, i.e., substitution of amino acids within groups of polar, non-polar, aromatic, charged, etc. amino acids. In the region of homology to the native sequence, variant polypeptides should have at least 90% similarity (preferably 90% identity), and within certain embodiments, greater than 92%, 95%, or 97% similarity (preferably 90–98% identity and all integer values in this range).

As is known in the art, "similarity" between two polypeptides is determined by comparing the amino acid sequence and conserved amino acid substitutes thereto of a polypeptide to the sequence of a second polypeptide. Fragments or portions of the polypeptides of the present invention may be employed for producing full-length polypeptide by, for example, peptide synthesis; therefore, the fragments may be employed as intermediates for producing the full-length polypeptides. Fragments or portions of the nucleic acids of the present invention may be used to synthesize full-length nucleic acids of the present invention. Amino acid and nucleic acid sequence similarity or identity may be determined by standard methodologies, including use of the National Center for Biotechnology Information BLAST search methodology available at www.ncbi.nlm.nih.gov. The polypeptide identity methodologies preferred are those described in U.S. Pat. No. 5,691,179 and Altschul et al., Nucleic Acids Res. 25:3389–3402, 1997, all of which are incorporated herein by reference. If Gapped BLAST 2.0 is utilized, then it is utilized with default settings.

A polynucleotide sequence encoding membrane derived caspase-3 polypeptide may be isolated from either genomic DNA or preferably cDNA. Isolation of a polynucleotide sequence encoding membrane derived caspase-3 from genomic DNA or cDNA typically may proceed by first generating an appropriate DNA library through techniques for constructing libraries that are known in the art (see Sambrook et al., *Molecular Cloning: A Laboratory Manual*, Cold Spring Harbor Press, 1989) or purchased from commercial sources (e.g., Clontech, Palo Alto, Calif.). Briefly, cDNA libraries can be constructed in bacteriophage vectors (e.g., λZAPII), plasmids, or other vectors that are suitable for screening, while genomic DNA libraries can be constructed in chromosomal vectors, such as YACs (yeast artificial chromosomes), bacteriophage vectors, such as λEMBL3, λgt10, cosmids, viral vectors, or plasmids. In certain preferred embodiments, cDNA libraries are made from cells with high caspase-3 activity.

In one embodiment, known caspase-3 gene sequences may be utilized to design an oligonucleotide hybridization probe suitable for screening genomic or cDNA libraries. Preferably, such oligonucleotide probes are 20–30 bases in length. To facilitate hybridization detection, the oligonucleotide may be conveniently labeled, generally at the 5' end, with a reporter molecule, such as a radionuclide, (e.g., $^{32}P$), enzymatic label, protein label, fluorescent label, or biotin. Such libraries are then generally plated as phage or colonies, depending upon the vector used. Subsequently, a nitrocellulose or nylon membrane, to which the colonies or phage have been transferred, is probed to identify candidate clones which contain the membrane derived caspase-3 gene. Such candidates may be verified as containing the target DNA by any of various means including, for example, DNA sequence analysis or hybridization with a second, non-overlapping probe.

Once a library is identified as containing a membrane derived caspase-3 gene, the gene can be isolated by amplification using, for example without limitation, the polymerase chain reaction. By way of illustration, a cDNA library may be used as a template for amplification with primers designed based upon known caspase gene sequences (sees e.g., GenBank Accession No. U13737 for caspase-3 and sequences available in the art). Primers may be annealed to the target DNA library and sufficient amplification cycles performed to yield a product readily visualized by gel electrophoresis and staining. The amplified fragment is purified and inserted into a vector, such as λgt10 or pBS (M13+), and propagated in a suitable host. Confirmation of the nature of the fragment may be obtained directly by DNA sequence analysis or indirectly by amino acid sequencing of the encoded polypeptide.

Primers for amplification are preferably derived from sequences in the 5' and 3' untranslated region in order to isolate a full-length cDNA. The primers preferably have a GC content of about 30%, more preferably about 40%, and most preferably about 50%. Restriction sites are typically incorporated into the primer sequences and, if necessary, translational initiation and termination codons can be engineered into the primer sequences. Due to the degeneracy in the genetic code, the membrane derived caspase-3 sequence derived from different sources may contain alternative codons encoding particular amino acids. Thus, the alternative codons for particular amino acids may be chosen as "optimal" for the host species chosen when, for example, generating synthetic DNA that encodes membrane derived caspase-3 polypeptide. As is known in the art and described herein, primers are designed to lack self-complementary sequences or complementary sequences at the 3' ends to prevent primer-dimer formation.

As will be appreciated by those skilled in the art, a nucleotide sequence encoding a caspase or variant may differ from the known native sequences due to, for example, codon degeneracies or nucleotide polymorphisms. In certain embodiments, variants should preferably hybridize to the native nucleotide sequence at conditions of medium stringency, which is approximately 25–30° C. below Tm of the native duplex (e.g., 5×SSPE, 0.5% SDS, 5×Denhardt's solution, 50% formamide, at 42° C. or equivalent conditions). As used herein, to "hybridize" under conditions of a specified stringency is used to describe the stability of hybrids formed between two single-stranded nucleic acid molecules. Stringency of hybridization is typically expressed in conditions of ionic strength and temperature at which such hybrids are annealed and washed (see, generally, Sambrook et al. *Molecular Cloning: A Laboratory Manual,* 2nd ed., Cold Spring Harbor Press, 1987; Ausubel et al., *Current Protocols in Molecular Biology*, Greene Publishing, 1987).

Other methods may also be used to obtain the membrane derived caspase-3 polypeptide encoding nucleic acid molecule. For example, a nucleic acid molecule encoding caspase may be obtained from an expression library by screening with an antibody or antibodies reactive to caspase-3 (see, Sambrook et al., *Molecular Cloning: A Laboratory Manual,* 2nd Ed., Cold Spring Harbor Laboratory Press, NY, 1987; Ausubel et al., *Current Protocols in Molecular Biology,* Greene Publishing Associates and Wiley-Interscience, NY, 1995; Srinivasan et al., Cell Death Differ. 12:1004, 1998).

A membrane derived caspase-3 polypeptide or functional fragment thereof may be produced by recombinant DNA methods. Accordingly, the invention provides an isolated nucleic acid molecule consisting essentially of a sequence encoding a membrane derived caspase-3 polypeptide of SEQ ID NO:3. In another preferred embodiment, the present invention relates to an isolated nucleic acid molecule encoding a membrane derived caspase-3 polypeptide consisting essentially of a single stranded or double stranded polynucleotide sequence of SEQ ID NO:2. Such an isolated nucleic acid molecule may be cloned into an appropriate vector for propagation, manipulation or expression as desired. Such a vector may be commercially available, may be constructed by those skilled in the art, or may contain expression elements necessary for the transcription, translation, regulation, and, if desired, sorting of the membrane derived caspase-3 polypeptide. The selected vector may also be used in a prokaryotic or eukaryotic host system, as appropriate, provided the expression and regulatory elements are of compatible origin. A recombinant membrane derived caspase-3 polypeptide or functional fragment thereof produced in a host cell or secreted from the cell can be isolated using, for example, an anti-caspase-3 antibody, as described herein.

A membrane derived caspase-3 polypeptide or functional fragment thereof may also be produced by chemical synthesis, for example, by the solid phase peptide synthesis method (Merrifield et al., *J. Am. Chem. Soc.* 85:2149 (1964)). Standard solution methods well known in the art also can be used to synthesize a membrane derived caspase-3 polypeptide or functional fragment thereof (Bodanszky, *Principles of Peptide Synthesis,* Springer-Verlag, Berlin (1984); Bodanszky, *Peptide Chemistry,* Springer-Verlag, Berlin, 1993). A newly synthesized membrane derived caspase-3 polypeptide or functional fragment thereof can be isolated, for example, by high performance liquid chromatography and can be characterized using mass spectrometry or amino acid sequence analysis.

Variants of a membrane derived caspase-3 gene may be engineered from natural variants (e.g., polymorphisms, splice variants, mutants), synthesized, or constructed. Many methods have been developed for generating mutants (see, generally, Sambrook et al., supra; Ausubel, et al., supra, and the discussion above). Briefly, preferred methods for generating a few nucleotide substitutions utilize an oligonucleotide that spans the base or bases to be mutated and includes the mutated base or bases. The oligonucleotide is hybridized to complementary single stranded or to one strand of denatured double stranded nucleic acid, and second strand synthesis is primed from the oligonucleotide. The double-stranded nucleic acid is prepared for introduction into suitable host cells, typically *E. coli,* but alternatively, other prokaryotes, yeast or other eukaryotes. Standard screening and vector amplification protocols are used to identify mutant sequences and obtain high yields of such sequences.

Similarly, deletions, insertions, and/or modifications of genes may be constructed by any of a variety of known methods as discussed supra. For example, a gene may be digested with a restriction enzyme(s) and religated such that a sequence is deleted, added or substituted. Other means of generating variant sequences may be employed with methods known in the art, for example, those described in Sambrook et al. (supra) and Ausubel et al. (supra). Verification of variant sequences is typically accomplished by restriction enzyme mapping, sequence analysis, or probe hybridization.

Such variants as well as fill-length forms of membrane derived caspase-3 may be used as tool in the analysis and identification of the protease responsible for novel cleavage at Lysine-14. While those of skill in the art can readily visualize a variety of assays to screen for this molecule, two of the most useful involve affinity, such as a yeast-two-hybrid assay or affinity chromatography, wherein short fragments of the N-terminus of membrane derived caspase-3 encompassing the lysine-14 cleavage site may be used as a probe for identifying the protease of interest.

B. Vectors, Host Cells, and Nucleic Acid Expression Vectors of Membrane Derived Caspase-3 Polypeptide A membrane derived caspase-3 polypeptide, such as the one encoded by the nucleotide sequence of SEQ ID NO:2, may be expressed in a variety of host organisms. In certain preferred embodiments, the polypeptide is expressed in mammalian cells (e.g., 697 lymphoblastoid cells, CHO, and COS-7), for which many expression vectors have been developed and are available. Other suitable host organisms include bacterial species (e.g., *E. coli, Bacillus subtilus, Salmonella typhimurium,* and *Pseudomonas aeruginosa*), and other eukaryotes, such as yeast (e.g., *Saccharomyces cerevisiae*), nematode cells and insect cells (e.g., Sf9).

The nucleic acid constructs of the present invention may be in the form of RNA or DNA, such as cDNA, genomic DNA, or synthetic DNA. DNA may be double stranded or single stranded, and if single stranded may be the coding or non-coding (anti-sense) strand. In particular preferred embodiments, a vector appropriate for a suitable host includes an isolated nucleic acid molecule encoding the membrane derived caspase-3 polypeptide consisting essentially of a single stranded or double stranded polynucleotide sequence of SEQ ID NO:2. The nucleic acid sequences that encode membrane derived caspase-3 polypeptide may include, but are not limited to, sequences comprising: only the coding sequence for membrane derived caspase-3 polypeptide; a coding sequence for membrane derived caspase-3 polypeptide and additional coding sequence; a coding sequence for membrane derived caspase-3 polypeptide (and optionally additional coding sequence) and a non-coding sequence, such as an intron or non-coding sequence 5' and/or 3' of the coding sequence for the membrane derived caspase-3 polypeptide (e.g., a regulatable promoter, enhancer, other transcription regulatory sequence, a repressor binding sequence, a translation regulatory sequence or any other regulatory nucleic acid sequence). Thus, the term "sequence encoding a membrane derived caspase-3 polypeptide" encompasses polynucleotides that may include coding sequence for the polypeptide as well as polynucleotides that include additional coding and/or non-coding sequence(s).

The present invention also relates to nucleic acid vectors and constructs that include nucleic acid sequences of the present invention, and in particular to "nucleic acid expression vectors" that include any polynucleotides encoding a membrane derived caspase-3 polypeptide as provided above. In a particularly preferred embodiment, the nucleic acid expression vector has a promoter operably linked to a polynucleotide encoding a membrane derived caspase-3 polypeptide. As used herein, a "promoter" refers to a nucleotide sequence that contains elements that direct the transcription of a linked gene and contains an RNA polymerase binding site. More typically, in eukaryotes, promoter sequences contain binding sites for other transcriptional factors that control the rate and timing of gene expression. Such sites may include a TATA box, CAAT box, POU box, AP1 binding site, and the like. Promoter regions may also contain enhancer elements. When at least one promoter is linked to a coding sequence so as to enable transcription of the coding sequence, it is "operably linked." Other regulatory sequences, alone or in combination, may be included on a nucleic acid expression vector, such as, without limitation, a transcription termination signal sequence, a secretion signal sequence, an origin of replication, a selectable marker, and the like. The regulatory sequences are operationally associated with one another to allow transcription or translation.

The expression vectors used herein include at least one promoter designed for expression of a polypeptide of interest in a host cell (e.g., E. coli or 697 lymphoblastoid cells). Suitable promoters are widely available and are well known in the art. In certain preferred embodiments there is a constitutive promoter, even more preferred is an iregulatable promoter, and most preferred is an inducible promoter. Such promoters for expression in bacteria include, for example, the T7, T3, T5, and SP6 phage promoters, and the trp, lpp, and lac operons. Hybrid promoters (see, U.S. Pat. No. 4,551,433), such as lacVV, tac, and trc, may also be used. Promoters for expression in eukaryotic cells include the P10 or polyhedron gene promoter of baculovirus/insect cell expression systems (see, e.g., U.S. Pat. Nos. 5,243,041, 5,242,687, 5,266,317, 4,745,051, and 5,169,784), LTR of the MMTV or RSV retroviruses, CMV IE promoter, SV40, metallothionein promoter (see, e.g., U.S. Pat. No. 4,870,009) and the like.

The promoter controlling transcription of the membrane derived caspase-3 gene may itself be controlled by a repressor. In some systems, the promoter can be derepressed by altering the physiological conditions of the cell, for example, by the addition of a molecule that competitively binds the repressor, or by altering the temperature of the growth media. Preferred repressor proteins include, but are not limited to, the E. coli LacI repressor responsive to IPTG induction, the temperature sensitive $\lambda$cI857 repressor, and the like. In other preferred embodiments, the vector also includes a transcription terminator sequence. A "transcription terminator region" has either a sequence that provides a signal that terminates transcription by the polymerase that recognizes the selected promoter and/or a signal sequence for polyadenylation.

One skilled in the art will appreciate that a wide variety of suitable vectors for expression in a particular host cell of choice are readily obtainable, including for example, plasmids, viruses, retrotransposons and cosmids. Nucleic acid expression vectors for bacterial use include, for example, the pET series (Novagen, Madison, Wis.), the tac and trc series (Pharmacia, Uppsala, Sweden), pTTQ18 (Amersham International plc, England), pACYC 177, pGEX series, and the like. The choice of a bacterial host for the expression of membrane derived caspsase-3 polypeptide is dictated in part by the vector and a person of ordinary skill in the art will know how to pair commercially available vectors with suitable hosts. Suitable vectors for expression in eukaryotic cells such as yeast, insect and mammalian cells include, for example, pCMVLacI, pXT1 (Stratagene Cloning Systems, La Jolla, Calif.); pCDNA series, pREP series, pEBVHis (Invitrogen, Carlsbad, Calif.). In certain embodiments, the gene of interest is cloned into a gene targeting vector, such as pMC1neo, a pOG series vector (Stratagene Cloning Systems). Baculovirus vectors, such as pBlueBac (see, e.g., U.S. Pat. Nos. 5,278,050, 5,244,805, 5,243,041, 5,242,687, 5,266,317, 4,745,051, and 5,169,784; available from Invitrogen, San Diego) may be used for expression in insect cells, such as Spodoptera frugiperda sf9 cells (see, U.S. Pat. No. 4,745,051).

The present invention provides coding sequence for membrane derived caspase-3 that may be inserted into a viral vector that may also function as a gene delivery vehicle, such as adenovirus, retrovirus, and the like. Representative examples include adenoviral vectors (e.g., WO 94/26914, WO 93/9191; Yei et al., Gene Therapy 1:192–200, 1994; Kolls et al., PNAS 91(1):215–219, 1994; Kass-Eisler et al., PNAS 90(24):11498–502, 1993; Guzman et al., Circulation 88(6):2838–48, 1993; Guzman et al., Cir. Res. 73(6) :1202–1207, 1993; Zabner et al., Cell 75(2):207–216, 1993; Li et al., Hum Gene Ther. 4(4):403–409, 1993; Caillaud et al., Eur. J. Neurosci 5(10):1287–1291, 1993), adeno-associated type 1 ("AAV-1") or adeno-associated type 2 ("AAV-2") vectors (see WO 95/13365; Flotte et al., PNAS 90(22):10613–10617, 1993), hepatitis delta vectors, live, attenuated delta viruses and herpes viral vectors (e.g., U.S. Pat. No. 5,288,641), as well as vectors which are disclosed within U.S. Pat. No. 5,166,320. Other representative vectors include retroviral vectors (e.g., EP 0 415 731; WO 90/07936; WO 91/02805; WO 94/03622; WO 93/25698; WO 93/25234; U.S. Pat. No. 5,219,740; WO 93/11230; WO 93/10218). For example, retroviruses from which a retroviral plasmid vector may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

In yet other embodiments, the coding sequence for membrane derived caspase-3 may be inserted into a vector such that a fusion protein is produced. By way of illustration and not limitation, membrane derived caspsase-3 polypeptide may be expressed as a hexa-his ($His_6$) fusion protein and isolated by metal-containing chromatography, such as nickel-coupled beads. Briefly, a sequence encoding $His_6$ is linked to a DNA sequence encoding the membrane derived caspsase-3 polypeptide. Although the $His_6$ sequence can be positioned anywhere in the molecule, preferably it is linked at the 3' end immediately preceding the termination codon. The fusion may be constructed by any of a variety of methods known in the art.

Preferably, the vector is capable of replication in the host cells. Thus, when the host cell is a bacterium, the vector preferably includes a bacterial origin of replication. Preferred bacterial origins of replication include the p15A, pSC101, and col E1 origins of replication, especially the ori derived from pUC plasmids. In yeast, ARS or CEN sequences can be used to assure replication. A well-known and often used system in mammalian cells is SV40 ori. With regard to plasmids, these vectors also preferably include at least one selectable marker that is functional in the host. A selectable marker gene includes any gene that confers a phenotype on the host that allows transformed cells to be identified and selectively grown. Suitable selectable marker genes for bacterial hosts include the ampicillin resistance gene ($Amp^r$), tetracycline resistance gene ($Tc^r$) and the kanamycin resistance gene ($Kan^r$). The kanamycin resistance gene is presently preferred. Suitable markers for eukaryotes usually require a complementary deficiency in the host (e.g., thymidine kinase (tk) in tk-hosts), although drug markers are also available (e.g., G418 resistance and hygromycin resistance).

The present invention provides a method of producing a membrane derived caspase-3 polypeptide by culturing a host cell containing a nucleic acid expression vector having at least one promoter operaby linked to a nucleic acid molecule encoding a membrane derived caspase-3 polypeptide, where the nucleic acid molecule consists essentially of SEQ ID NO:2. Such host cells are cultured under conditions and for a time sufficient for expression of the polypeptide and a membrane fraction (e.g., preferred fractions would include nuclear or heavy membranes) is isolated from the intact host cells as provided herein. In certain preferred embodiments, the nucleic acid expression vector used to produce the membrane derived caspsase-3 polypeptide has an inducible promoter.

Within certain aspects of the invention, isolated nucleic acid molecules that encode membrane derived caspase-3 polypeptide consisting essentially of a sequence of SEQ ID NO:3 may be introduced into a host cell by utilizing a gene delivery vehicle or various physical methods as described herein. Representative examples of such methods include transformation using calcium phosphate precipitation for eukaryotic cells (Dubensky et al., *PNAS* 81:7529–7533, 1984) and calcium chloride or magnesium chloride for prokaryotic cells (see Sambrook, supra), direct microinjection into intact target cells (Acsadi et al., *Nature* 352:815–818, 1991), and electroporation whereby cells suspended in a conducting solution are subjected to an intense electric field in order to transiently polarize the membrane, allowing entry of the nucleic acid molecules. Other procedures include the use of isolated nucleic acid molecules encoding membrane derived caspase-3 linked to an inactive adenovirus (Cotton et al., *PNAS* 89:6094, 1990), lipofection (Felgner et al., *Proc. Natl. Acad. Sci. USA* 84:7413–7417, 1989), microprojectile bombardment (Williams et al., *PNAS* 88:2726–2730, 1991), polycation compounds such as polylysine, receptor specific ligands to induce receptor mediated endocytosis, liposomes entrapping the nucleic acid molecules, spheroplast fusion whereby *E. coli* containing the nucleic acid molecules are stripped of their outer cell walls and fused to animal cells using polyethylene glycol, viral transduction, (Cline et al., *Pharmac. Ther.* 29:69, 1985; and Friedmann et al., *Science* 244:1275, 1989), and use of a DNA ligand (Wu et al., *J. Biol. Chem.* 264:16985–16987, 1989), as well as psoralen inactivated viruses such as Sendai or Adenovirus.

Some preferred embodiments, for example, include a gene delivery vehicle associated with a polycation, a gene delivery vehicle that further includes a ligand that binds a cell surface receptor, and a gene delivery vehicle having an isolated nucleic acid encoding a membrane derived caspase-3 polypeptide consisting essentially of a sequence of SEQ ID NO:2 that is operably linked to a promoter. The present invention would be particularly useful for the treatment of apoptosis related diseases, such as bacterial infections, viral infections, cancer, and autoimmune disease. For example, the desired composition may be by administering such that the gene delivery vehicle, nucleic acid expression construct, polypeptide or the like are internalized by the host cell mediating the targeted disease (i.e., cancer or autoimmune disease) or the host cell that is infected by a pathogen (i.e., bacterially- or virally-infected). It is well established in the art that some bacterial pathogens that associate with or invade eukaryotic cells (e.g., Shigella, Salmonella, and Streptococcus species and *E.coli*) and viral pathogens (e.g., HIV, HTLV, and HCV) may induce apoptosis.

As noted above and described herein, cells synthesize caspases as inactive zymogens (procaspases), which are converted into active caspases when they are cleaved at specific aspartic acid residues to release mature large and small subunits. The activated caspases in turn proteolytically activate downstream procaspases, such as procaspase-3. Similar to the cytoplasmic caspase-3, the membrane derived caspase-3 polypeptide must also be cleaved for activation. A surprising result of the present invention is that a membrane fraction containing membrane derived caspase-3 polypeptide is capable of slowly and spontaneously (i.e., in the absence of a caspase activator) activating and that rapid activation occurs in the presence of a caspase activator.

Thus, in certain preferred embodiments, membrane fractions (e.g., nuclear or heavy membrane fractions) may be contacted with a caspase activator under conditions and for a time sufficient to activate the membrane derived caspase-3 polypeptide. In other preferred embodiments, the membrane derived caspase-3 polypeptide activator used may be selected, without limitation, from caspase-1, caspase-8, caspase-9, caspase-10, and Granzyme B. In yet other embodiments, the membrane fraction may be solubilized with detergent, before or after activation. Detergents that may be used with the present invention include without limitation Triton X-100, β-octyl glucoside, and CHAPS.

A person of skill in the art will appreciate that the enzymatic activation reaction necessarily requires a protein—protein interaction. Similarly, active caspases exist as tetrameric oligomers comprised of two large and two small subunits. As used herein, "oligomerize" indicates that at least one polypeptide associates with at least one other polypeptide. The oligomerization may be between identical or substantially similar polypeptides (homooligomers) or between different polypeptides (heterooligomers). The interaction or association that constitutes an oligomerization may result from a typical ligand-receptor interaction or other electrostatic interaction, hydrophobic interaction, permanent or transient covalent interaction, and the like. The oligomerization may be permanent, semi-permanent (e.g., the quaternary structure that results when active caspase oligomerizes into a tetramer), or transient (e.g., oligomerization resulting in an enzymatic reaction). In a preferred embodiment, a membrane derived caspase-3 polypeptide of SEQ ID NO:3 may oligomerize with a caspase. In one embodiment, the membrane derived caspase-3 polypeptide may oligomerize with other membrane derived caspase-3 polypeptides, and in other embodiments the membrane derived caspase-3 polypeptide may oligomerize with other caspases, such as caspase-1, caspase-2, caspase-3 (cytoplasmic), caspase-4, caspase-5, caspase-6, caspase-7, caspase-8, caspase-9, caspase-10, caspase-11, caspase-12, caspase-13, and caspase-14. In addition, membrane derived caspase-3 polypeptides may oligomerize with apoptosis proteins, such as Apaf-1 and Bcl-2, or other cellular proteins, such as those involved in DNA replication, DNA repair, RNA splicing, protein phosphorylation, and apoptotic chromosomal fragmentation.

The membrane derived caspsase-3 polypeptide or any other apoptosis related polypeptide produced by the methods described herein may be isolated by standard methods, such as affinity chromatography, size exclusion chromatography, metal ion chromatography, ionic exchange chromatography, HPLC, and other known protein isolation methods (see, generally, Ausubel et al. supra; Sambrook et al supra). As noted above and described herein, caspases typically recognize an Asp-Glu-Val-Asp (DEVD; SEQ ID NO:6) tetrapeptide as a substrate (cleaving between the Val and Asp), but the addition of aldehyde (DEVDalde) inhibits the cleavage reaction and the DEVDalde, therefore, may function as an affinity reagent that binds caspase. Thus, by way of illustration and not limitation, a streptavidin agarose (Sigma, St. Louis, Mo.) column charged with biotinyl-DEVDaldehyde affinity reagent may be used to isolate membrane derived caspsase-3 polypeptide from nuclear or heavy membrane preparations. Typically, an isolated polypeptide may be visualized as a single band by SDS-PAGE when stained with Coomassie blue or when reacted with a primary antibody directed to membrane derived caspsase-3 polypeptide and a labeled secondary antibody directed to the primary antibody.

C. Membrane Preparations

Membrane preparations within the context of the present invention may be derived from a variety of cell types or sources. Typically, for ease of handling, the cells utilized will be an eukaryotic cell line or other culturable cell type. However, cells can also be derived from tissues and other non-cultured sources. One of ordinary skill in the art would readily appreciate that the assays of the present invention are not dependent upon the exact source or type of cell from which membrane fractions are prepared.

Subcellular fractionation has been a basic research tool in cell biology for the last 30 years. Accordingly, those of ordinary skill in the art are familiar with various techniques for such fractionation. Typically, subcellular fractionation comprises two basic steps, 1) homogenization and 2) separation. Homogenization in its ideal form allows particulate organelles such as the nucleus, mitochondria, lysosomes, and peroxisomes to remain intact. A variety of homogenization techniques are known, such as Dounce homogenizers (glass/glass), Potter-Elvehjem homogenizers (glass/Teflon), repeated pipetting, passage through small gauge needle, and the like. Exemplary techniques, incorporated by reference, are described in detail by Harms et al., *Proc. Natl. Acad. Sci. USA* 77:6139–6143 1980, Darte et al., *J. Exp. Med.* 157:1208–1228, 1983, and Balch et al., *Cell* 39:405–416, 1984.

Separation of subcellular fractions is traditionally performed using density gradients. While sucrose gradients are the most widely used, many other alternatives are available (e.g., Ficoll, Percoll, Metrizamide, and Nycodenz) (see Methods in Enzymology Vol 31, Part A (Flescher and Packer eds.), 1974). In addition, a number of alternative methods have been developed for isolation of various components, including density modification, free flow electrophoresis, and immuno-isolation (see Cell free Analysis of Membrane Traffic, pp. 35–127, (Morre et al. eds.)(1988)). Moreover, a variety of references are available which detail a multitude of fractionation techniques, for example, see Methods in Enzymology Vol. 31, Part A (Flescher and Packer eds.), 1974; Partition of Cell Particles and Macromolecules: Separation and purification of Biomolecules, Cell Organelles, Membranes, and Cells (Albertsson, ed.), 1986; Martin et al., *Eur. J. Clin. Inv.* 13:49–56, 1983.

An exemplary method of cellular fractionation comprises suspending cells in a hypotonic buffer in which a variety of protease inhibitors are present (e.g., PMSF, leupeptin, pepstatin, aprotinin, EDTA, etc.). The samples are incubated on ice, then homogenized using, for example, a Dounce homogenizer. Following homogenization the homogenate is centrifuged at 500×g to separate nuclei. The nuclear pellet can then be washed and resuspended. The supernatant is then centrifuged at 14,000×g for 30 minutes to pellet the heavy membranes. The 14,000×g supernatant can then be centrifuged at 100,000×g for 30 minutes to yield a supernatant (cytoplasmic fraction) and a pellet (light membrane fraction). Each pelleted fraction can then be washed and resuspended in the appropriate buffer for assaying. A skilled artisan will appreciate that subcellular fractions may vary somewhat in content, but that well known exemplary markers (e.g., cytochrome oxidase for mitochondria, poly(ADP-ribose) polymerase (PARP) for nuclei, D4-GDP dissociation inhibitor (D4-GDI) for the cytoplasm, and Bcl-2 for membranes) may be utilized to characterize each subcellular fraction prepared by any methodology to establish that each fraction will reproducibly contain the specific activity of interest.

D. Antibodies, Assays, and Treatment Methods

Antibodies that specifically bind to a particular membrane derived caspase-3 polypeptide, variant, or functional fragment thereof may be used to purify the polypeptide from natural sources using well known techniques and readily available starting materials. Such antibodies may also be used to purify the membrane derived caspase-3 polypeptide from material present when producing the polypeptide by recombinant DNA methodology. The present invention relates to an antibody that is specific for a membrane derived caspase-3 polypeptide consisting essentially of SEQ ID NO:3. In certain embodiments, the invention provides antibodies that specifically bind to membrane derived caspase-3 polypeptide-specific epitopes. Such membrane derived caspase-3 polypeptide-specific epitopes are present in membrane derived caspase-3 polypeptides and functional fragments thereof, but not in other caspase polypeptides or vice versa, including cytoplasmic caspase-3. As an illustration, the epitope for the antibody may comprise a sequence overlapping the lysine 14 cleavage site, wherein the presence of sequences N-terminal to this lysine residue allow for detection while the absence does not. Such an antibody could be used to compare levels of caspase-3 detected by other antibodies that react with shared epitopes of membrane derived caspase-3 and cytoplasmic caspase-3, thereby allowing for the estimation of membrane derived caspase-3 in a sample. Antibodies that bind membrane derived caspase-3 polypeptide-specific epitopes may be readily identified by their inability to cross react with other caspases, cytoplasmic caspase-3, and the like.

A membrane derived caspase-3 polypeptide or functional fragment thereof may comprise an immunogenic amino acid sequence or, if haptenic, may be conjugated to another molecule to become immunogenic, as described below. The sequence length to be used may vary depending on the desired use, but will preferably comprise at least 8 contiguous amino acids of membrane derived-caspase-3 or its cytoplasmic form or at least enough contiguous amino acids to facilitate an immunogenic response either when conjugated to another molecule or when utilized in a non-conjugated form. Thus, a membrane derived caspase-3 polypeptide may be useful for eliciting production of an anti-membrane derived caspase-3 antibody. In addition, the invention provides a cell expressing an anti-membrane derived caspase-3 polypeptide antibody, such as a monoclonal antibody. Further, it should be understood that an antibody specific for a membrane derived caspase-3 refers broadly to the ability to detect the presence of a membrane derived caspase-3 and includes, for example, antibodies that bind cytoplasmic caspase-3, but lose recognition of cytoplasmic caspase-3 once processed to the membrane derived form. Accordingly, specificity, while including the ability to bind specific epitopes, also refers to the ability of an antibody to specifically lose binding ability when an epitope is lost, thus allowing for detection of the presence of the membrane derived caspase. Alternatively, the antibody may specifically bind membrane derived caspase-3 and not caspase-3 overall based on an exposed epitope that exists on the membrane derived caspase-3 and not others. Persons having skill in the art understand that such antibodies exist; for example, there are antibodies that specifically bind mature caspase (e.g., $CM_1$) and not procaspase.

As used herein, the term "antibody" is used in its broadest sense to include polyclonal, monospecific, and monoclonal antibodies, as well as antigen binding fragments of such antibodies. With regard to an anti-membrane derived caspase-3 antibody of the invention, the term "antigen" means a membrane derived caspase-3 polypeptide, variant, or functional fragment thereof. An anti-membrane derived caspase-3 antibody, or antigen binding fragment of such an antibody, may be characterized as having specific binding activity for a membrane derived caspase-3 polypeptide or epitope thereof of at least about $1 \times 10^5$ $M^{-1}$, generally at least about $1 \times 10^6$ $M^{-1}$, and preferably at least about $1 \times 10^8$ $M^{-1}$. Fab, F(ab')$_2$, Fd and Fv fragments of an anti-membrane derived caspase-3 antibody, which retain specific binding activity for a membrane derived caspase-3 polypeptide-specific epitope, are encompassed within the anti-membrane derived caspase-3 antibody of the invention.

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof Such non-naturally occurring antibodies may be constructed using solid phase peptide synthesis, may be produced recombinantly, or may be obtained, for example, by screening combinatorial libraries consisting of variable heavy chains and variable light chains (Huse et al., *Science* 246:1275–1281 (1989)). These and other methods of making, for example, chimeric, humanized, CDR-grafted, single chain, and bifunctional antibodies are well known in the art (Winter and Harris, *Immunol. Today* 14:243–246 (1993); Ward et al., *Nature* 341:544–546 (1989); Harlow and Lane, *Antibodies: A Laboratory Manual*, Cold Spring Harbor Laboratory, New York (1992); Borrabeck, *Antibody Engineering*, 2d ed., Oxford Univ. Press (11995); Hilyard et al., *Protein Engineering: A practical approach*, IRL Press (1992)).

In certain preferred embodiments, an anti-membrane derived caspase-3 antibody may be raised using as an immunogen such as, for example, an isolated membrane derived caspase-3 polypeptide consisting essentially of SEQ ID NO:3, which may be prepared from natural sources or produced recombinantly, as described above, or a functional fragment of a membrane derived caspase-3 polypeptide (e.g., immunogenic sequences comprising those contiguous amino acid sequences N-terminal of Lysine-14, which may or may not include pro-domain sequences), including synthetic peptides, as described above. A non-immunogenic peptide portion of a functional fragment of a membrane derived caspase-3 polypeptide can be made immunogenic by coupling the hapten to a carrier molecule such as bovine serum albumin (BSA) or keyhole limpet hemocyanin (KLH), or by expressing the peptide portion as a fusion protein. Various other carrier molecules and methods for coupling a hapten to a carrier molecule are well known in the art (Harlow and Lane, supra, 1992).

For example and without wishing to be bound by theory, an anti-membrane derived caspase-3 antibody is useful for determining the presence or level of membrane derived caspase-3 polypeptide in a tissue sample, which may be a cell lysate or a histological section. The identification of the presence or level of membrane derived caspase-3 polypeptide in a sample can be made using well known immunoassay and immunohistochemical methods (Harlow and Lane, supra, 1992). Additionally, an anti-membrane derived caspase-3 antibody can be used in a screening assay to identify agents that alter the activity of membrane derived caspase-3 polypeptide or that alter the binding of membrane derived caspase-3 polypeptide to a second protein.

As noted above and described herein, it is generally accepted in the art that cytoplasmic caspase-3 activation is caused by cleavage of the zymogen after the Asp 175 residue, which causes the liberation of the mature small subunit. Further, as described herein for the present invention, activation of membrane derived caspase-3 polypeptide by a caspase such as caspase-1 may also occur by the same mechanism because the Ile174-Asp177 site of SEQ ID NO:3 appears to be the most similar to the canonical caspase-1 cleavage site identified by substrate specificity studies (see, e.g., Talanian et al., J. Biol. Chem. 272:9677, 1997; SEQ ID NO:1). Thus, activation of membrane derived caspase-3 may result in the partial or complete release of the small and large subunits from the membrane into, for example, the cytoplasm. In contrast to the small subunit, the large subunit for cytoplasmic caspase-3 may arise via a different mechanism than does the membrane derived caspase-3 large subunit. The N-terminal residue of the large subunit of cytoplasmic caspase-3 may be Ser 10 or Ser 29, whereas the N-terminal residue of the large subunit of activated, purified membrane derived caspase-3 is Lys 14. Thus, the invention relates in part to the surprising discovery that membrane derived caspase-3 is activated at a novel processing site that is not after an aspartic acid residue and possibly by a novel mechanism. As is generally accepted in the art, cytoplasmic caspase activation typically occurs by cleavage after Asp 9 or Asp 28. Without wishing to be bound by theory, the membrane derived caspase-3 large subunit may be generated by cleavage after Asp 9 with residues 10–13 being removed by a second protease, or, alternatively, membrane derived caspase-3 polypeptide might be cleaved specifically after Ile 13 by a novel membrane-associated or cytoplasmic protease, or by an auto-catalytic reaction.

Accordingly, the anti-membrane derived caspase-3 antibodies of the present invention include an antibody that does not specifically recognize a cytoplasmic derived caspase-3 and does specifically recognize a membrane derived caspase-3 polypeptide, the membrane derived caspase-3 polypeptide consisting essentially of SEQ ID NO:3. Additionally, the antibodies of the present invention include an antibody that specifically recognizes a cytoplasmic derived caspase-3 and does not specifically recognize a membrane derived caspase-3 polypeptide, the membrane derived caspase-3 polypeptide consisting essentially of SEQ ID NO:3. For example, these antibodies are particularly useful for monitoring the distribution of cytoplasmic and membrane derived caspase-3 in both cells undergoing and not undergoing apoptosis, or in cells or biological samples derived from patients suffering from apoptosis related diseases such as cancer or autoimmune disease.

In certain other embodiments, a particularly useful anti-membrane derived caspase-3 antibody is one that binds a membrane derived caspase-3 polypeptide, such as SEQ ID NO:3, but not to either the large or small subunit cleavage products of the membrane derived caspase-3 polypeptide, such as amino acid positions 1 to 70 of SEQ ID NO:3, as well as the corresponding large and small subunits of splice variant isoforms. In yet other embodiments, an antibody that binds to either the large subunit or the small subunit of a membrane derived caspase-3 polypeptide, but not to the other subunit or the membrane derived caspase-3 polypeptide, as well as an antibody that binds to a heterodimer comprising the large subunit and the small subunit of a membrane derived caspase-3 polypeptide or a heterotetramer, but not to the membrane derived caspase-3 polypeptide, is useful. An antibody that binds a membrane derived caspase-3 polypeptide may be useful to isolate membrane derived caspase-3 polypeptide from a sample, whereas an antibody that binds the large subunit or the small subunit of a membrane derived caspase-3 polypeptide may be useful to identify samples with caspase-3 processing activity. An antibody that binds a membrane derived caspase-3 subunit heterodimer or heterotetramer may be useful to isolate membrane derived caspase-3 with apoptotic activity or in a screening assay to identify, for example, an agent that inhibits heterodimer or heterotetramer formation and, therefore, apoptosis. For convenience, reference herein to an anti-membrane derived caspase-3 antibody generally includes all such antibodies, although the skilled artisan will recognize that the choice of a particular antibody will depend on the purpose for which the antibody will be used.

A kit incorporating an anti-membrane derived caspase-3 antibody can be particularly useful. Such a kit may contain, in addition to an anti-membrane derived caspase-3 antibody, a reaction cocktail that provides the proper conditions for performing the assay, control samples that contain known amounts of membrane derived caspase-3 polypeptide, or other appropriate membrane derived caspase-3 antigen recognized by the antibody and, if desired, a second antibody specific for the anti-membrane derived caspase-3 antibody. Such an assay may also include a simple method for detecting the presence or amount of membrane derived caspase-3 polypeptide in a sample that is bound to the anti-membrane derived caspase-3 antibody.

An anti-membrane derived caspase-3 antibody, as well as a membrane derived caspase-3 polypeptide or functional fragment thereof, may be labeled so as to be detectable using methods well known in the art (Hermanson, *Bioconjugate Techniques*, Academic Press (1996); Harlow and Lane, supra, 1992). For example, an anti-membrane derived caspase-3 antibody may be labeled with various detectable moieties including a radiolabel, an enzyme, biotin, or a fluorochrome. Reagents for labeling an anti-membrane derived caspase-3 antibody may be included in a kit containing the antibody or can be purchased separately from a commercial source.

Following contact, for example, of a labeled antibody with a sample such as a tissue homogenate or a histological section of a tissue, specifically bound labeled antibody can be identified by detecting the particular moiety attached as a detectable marker. Alternatively, a labeled second antibody can be used to identify specific binding of an unlabeled anti-membrane derived caspase-3 antibody. A second antibody generally will be specific for the particular class of the first antibody. For example, if art anti-membrane derived caspase-3 antibody is of the IgG class, a second antibody will be an anti-IgG antibody. Such second antibodies are readily available from commercial sources. and the second antibody may be labeled using a detectable moiety as described above. For example, when a sample is labeled using a second antibody, the sample is first contacted with a first antibody, which is an anti-membrane derived caspase-3 antibody, then the sample is contacted with the labeled second antibody, which specifically binds to the anti-membrane derived caspase-3 antibody and results in a labeled sample.

Methods for raising polyclonal antibodies, for example, in a rabbit, goat, mouse or other mammal, are well known in the art. In addition, monoclonal antibodies may be obtained using methods that are well known and routine in the art (Harlow and Lane, supra, 1992). For example, spleen cells from a membrane derived caspase-3 polypeptide-immunized mammal can be fused to an appropriate myeloma cell line such as SP/02 myeloma cells to produce hybridoma cells. Cloned hybridoma cell lines may be screened using a labeled membrane derived caspase-3 polypeptide or functional fragment thereof to identify clones that secrete anti-membrane derived caspase-3 monoclonal antibodies having the desired specificity. Hybridomas expressing anti-membrane derived caspase-3 monoclonal antibodies having a desirable specificity and affinity may be isolated and utilized as a continuous source of the antibodies, which are useful, for example, for preparing standardized kits as described above. Similarly, a recombinant phage that expresses, for example, a single chain anti-membrane derived caspase-3 also provides a monoclonal antibody that may be used for preparing standardized kits.

A monoclonal anti-membrane derived caspase-3 antibody may be used to prepare anti-idiotypic antibodies, which present an epitope that mimics a membrane derived caspase-3-specific epitope recognized by the monoclonal antibody used to prepare the anti-idiotypic antibodies. Where the epitope mimicked includes, for example, a portion of the membrane derived caspase-3 catalytic domain, the anti-idiotypic antibody can act as a competitor of membrane derived caspase-3 polypeptide activity and, therefore, can be useful for reducing the level of membrane derived caspase-3 polypeptide activity and, consequently, the level of apoptotic activity. Thus, the invention further provides an anti-idiotypic anti-membrane derived caspase-3 antibody, which mimics a membrane derived caspase-3-specific epitope, an epitope of the large or small subunit of a membrane derived caspase-3 polypeptide, or an epitope of a membrane derived caspase-3 heterodimer or heterotetramer.

The present invention also pertains to a membrane derived caspase-3 polypeptide or functional fragment thereof that may induce apoptosis or be part of a heterodimeric or a heterotetrameric apoptotic complex. Conversely, a membrane derived caspase-3 inhibitor such as the large subunit of membrane derived or cytoplasmic caspase-3 that lacks the active site QACRG (SEQ ID NO:5; positions 148–152 of SEQ ID NO:3), for example, can bind the small subunit of membrane derived caspase-3 and prevent an active protease complex from forming. Thus, a membrane derived caspase-3 polypeptide may be screened, for example, for inducing or enhancing apoptosis and an inhibitor of membrane derived caspase-3 activity may be screened for inhibiting or repressing apoptosis. A particularly preferred embodiment is a method of inducing apoptosis in a cell by delivering to a cell an effective amount of an isolated nucleic acid molecule encoding a membrane derived caspase-3 polypeptide, where the nucleic acid molecule consists essentially of SEQ ID NO:2, and culturing under conditions and for a time sufficient for expression of the membrane derived caspase-3 polypeptide. Another embodiment includes a method of inducing apoptosis in a cell by delivering to a cell an effective amount of membrane derived caspase-3 polypeptide, where the nucleic acid molecule consists essentially of SEQ ID NO:2, and culturing under conditions and for a time sufficient to detect the induction of apoptosis. A preferred mode of delivery to a cell of membrane derived caspase-3 polypeptide includes injecting (e.g., microinjection as described herein supra) the polypeptide. As used herein, an "effective amount" is that amount required to achieve a desired result. Methods known in the art and described herein may be used to detect whether the cell is undergoing apoptosis.

As used herein, "inducing apoptosis" is the ability either alone, or in combination with another molecule, to promote programmed cell death accompanied by at least one of the morphological or biochemical alterations characteristic of apoptosis. Morphological and biochemical alterations characteristic of apoptosis are well known in the art. For example, morphological alterations include without limitation condensed and rounded cellular morphology; membrane blebbing; the formation of apoptotic bodies, which are membrane-bound bodies containing cytoplasmic and nuclear components; and condensation of the nucleus, with cytoplasmic organelles being relatively well maintained (Cohen, Gerald, supra, 1997; Studzinski (Ed.), *Cell Growth and Apoptosis*, Oxford: Oxford University Press (1995)). Biochemical alterations include the typical appearance of oligonucleosome-sized fragments of DNA, which produce a "ladder" upon agarose gel electrophoresis. This extensive nucleic acid fragmentation may be preceded by an earlier endonucleolytic cleavage of chromatin, producing, for example, DNA fragments of about 50 kb to 300 kb in size. As described herein, other biochemical characteristics of apoptosis include, without limitation, annexin binding and release of cytochrome c from mitochondria.

A variety of assays for determining whether a membrane derived caspase-3 polypeptide or functional fragment thereof has apoptotic activity or whether a membrane derived caspase-3 inhibitor has anti-apoptotic activity are well known in the art. Such methods include light microscopy for determining the presence of one or more morphological characteristics of apoptosis, such as condensed or rounded morphology, shrinking and blebbing of the cytoplasm, preservation of structure of cellular organelles including mitochondria, and condensation and margination of chromatin. Within another apoptosis assay, translocation of cell membrane phosphatidylserine (PS) from the inner to the outer leaflet of the plasma membrane may be evaluated by measuring outer leaflet binding by the PS-specific protein annexin (Martin et al., *J. Exp. Med.* 182:1545, 1995; Fadok et al., *J. Immunol.* 148:2207, 1992).

A membrane derived caspase-3 polypeptide or functional fragment thereof or a membrane derived caspase-3 inhibitor may also be assayed for respective apoptotic or anti-apoptotic activity using terminal deoxytransferase-mediated (TdT) dUTP biotin nick end-labeling (TUNEL) (Gavriel et al., *J. Cell Biol.* 119:493 (1992); Gorczyca et al., *Int. J. Oncol.* 1:639 (1992); Studzinski, supra, 1995). APOPTAG (ONCOR, Inc.; Gaithersburg Md.) is a commercially available kit for identification of apoptotic cells using digoxygenin labeling. In addition, a membrane derived caspase-3 polypeptide or a membrane derived caspase-3 inhibitor may be assayed for respective apoptotic or anti-apoptotic activity by detecting nucleosomal DNA fragments using agarose gel electrophoresis (Studzinski, supra, 1995; Gong et al., *Anal. Biochem.* 218:314 (1994)).

A further apoptosis assay is based on detection of the mitochondrial protein cytochrome c that has been released by mitochondria in an apoptotic cell (Liu et al., *Cell* 86:147, 1996). Such detection of cytochrome c may be performed spectrophotometrically, immunochemically, or by other well established methods for determining the presence of a specific protein. Matrix-assisted laser desorption ionization time-of-flight (MALDI-TOF) mass spectrometry coupled with affinity capture is particularly suitable for such analysis since apo-cytochrome c and holo-cytochrome c can be distinguished on the basis of their unique molecular weights. For example, the Surface-Enhanced Laser Desorption/Ionization (SELDI™) system (Ciphergen, Palo Alto, Calif.) may be used to determined the effect of membrane derived caspase-3 polypeptide or membrane derived caspase-3 inhibitor on cytochrome c release from mitochondria. In this approach, a cytochrome c specific antibody immobilized on a solid support is used to capture released cytochrome c present in a soluble cell extract. The captured protein is then encased in a matrix of an energy absorption molecule (EAM) and is desorbed from the solid support surface using pulsed laser excitation. The molecular mass of the protein is determined by its time of flight to the detector of the SELDI™ mass spectrometer.

An additional apoptosis assay involves DNA filter elution methodology to detect apoptosis-associated DNA fragmentation and to determine apoptotic or anti-apoptotic activity (Studzinski, supra, 1995; Bertrand et al., *Drug Devel.* 34:138 (1995)). Apoptotic or anti-apoptotic activity also may be detected and quantitated by determining an altered mitochondrial to nuclear DNA ratio as described in Tepper et al., *Anal. Biochem.* 203:127 (1992) and Tepper and Studzinski, *J. Cell Biochem.* 52:352 (1993). One skilled in the art understands that these and other assays for apoptotic or anti-apoptotic activity may be performed using routine methodology.

The apoptosis assays of the present invention may be conducted as in vitro assays (e.g., using cell fractions) or in vivo assays (e.g., using suitable host cells). The in vivo assays may performed by using suitable host cells, such as primary cell lines, immortalized tissue culture cell lines, or using a warm-blooded mammalian where the host cell is located. In one preferred embodiment the host cell used comprises a tissue culture cell, including without limitation 697 lymphoblastoid cells, E15 primary brain cortical cells, MN9D cells, Jurkat T cells, THP-1 cells, FL5. 12 cells, and the like.

Furthermore, the present invention pertains to a method for identifying an agent that alters the activity of a membrane derived caspase-3 polypeptide. In a preferred embodiment, the method for identifying an agent that alters the activity of a membrane derived caspase-3 polypeptide consisting essentially of SEQ ID NO:3 includes contacting the membrane derived caspase-3 polypeptide with a caspase substrate in the presence and absence of at least one candidate agent, and comparing the levels of caspase substrate turnover to identify an agent that alters the activity of the membrane derived caspase-3 polypeptide. Candidate agents may be isolated or procured from a variety of sources, such as bacteria, fungi, plants, parasites, libraries of chemicals, peptides or peptide derivatives and the like. The agents may function as inhibitors or enhancers, and may be also be rationally designed based on the protein structure determined from X-ray crystallography (see, Mittl et al., *J. Bio. Chem.*, 272:6539–6547, 1997). In certain embodiments, the agent inhibits a membrane derived caspase-3 or functional fragment thereof. In another embodiment, the candidate agent may indirectly affect the release/evolution of membrane derived caspase activity.

Without being held to a particular mechanism, an inhibitor agent may act by preventing processing of a caspase, preventing caspase enzymatic activity by other mechanisms, or by preventing dissociation of the membrane derived caspase-3 from the membrane. Accordingly, the inhibitor agent may act directly or indirectly. In one embodiment, inhibitors interfere in the processing of the caspase protein. In other embodiments, the inhibitors are small molecules. In yet another embodiment, inhibitors interact with Bcl-2. In other aspects, the inhibitors prevent apoptosis. Inhibitors should have a minimum of side effects and are preferably non-toxic. Inhibitors that can penetrate cells are preferred.

In addition, enhancer agents of membrane derived caspase-3 activity or expression are desirable in certain circumstances. At times, increasing apoptosis will have a therapeutic effect. For example, tumors or cells that mediate autoimmune diseases are appropriate cells for destruction. Enhancers may increase the rate or efficiency of caspase processing, increase transcription or translation, increase caspase release/evolution from the membrane, or act through other mechanisms. As is apparent to one skilled in the art, many of the guidelines presented above apply to the design of enhancers as well.

Screening assays for candidate agents will vary according to the type of agent and the nature of the activity that is being affected. In general, assays, within the context of the present invention, are designed to evaluate membrane derived caspase-3 polypeptide activity. In any of the assays, a statistically significant increase or decrease compared to a proper control is indicative of enhancement or inhibition. Moreover, it should be understood that detection of membrane derived caspase-3 activity may be by direct or indirect means. For example, a direct means is detecting membrane derived caspase-3 substrate turnover, while an indirect means may detect the processing or direct activity of another caspase activated by the membrane derived caspase-3.

In one embodiment, the assay utilizes membrane preparations from eukaryotic cells. In this regard, any cell type may be used depending on the purpose of the assay. In certain embodiments, the membrane fraction comprises heavy membranes and/or nuclear membranes. In one aspect, the membrane fraction is contacted or contacted and incubated in the presence or absence of a candidate agent and the substrate turnover or caspase-processing is measured. Substrate turnover or caspase-processing (cleavage of caspases into large and small subunits) can be assessed by a variety of methods known by those of skill in the art including, for example, fluorescence spectroscopy, mass spectroscopy, HPLC, colorimetry (e.g., UV and visible spectroscopy), fluorography, radiography, gel electrophoresis, immunoblotting/immuno-affinity, chromatography, N-terminal peptide sequencing and the like. Moreover, one of ordinary skill in the art will recognize that incubation may be carried out at a variety of temperatures, depending on the kinetics to be studied. In one embodiment, the incubation temperature is from 20° C. to 40° C. In other embodiments, the incubation temperature is from 25° C. to 37° C.

One in vitro assay can be performed by examining the effect of a candidate agent on the processing of a caspase (e.g., a pro-caspase or other protein substrate of a caspase) into two subunits. Briefly, a substrate (e.g., peptide, protein, or peptide mimetic) containing the enzyme recognition site of membrane derived caspase-3 is utilized (e.g., DEVD), for example, when such a substrate is a protein or peptide, the substrate is in vitro translated or purified from a cell expression system. This primary product is contacted or contacted and incubated with the membrane fraction in the presence or absence of a candidate agent and assessed for appearance of the two subunits. To facilitate detection, typically, the protein or peptide is labeled during translation or via gene fusion prior to expression. If radiolabeled, the two subunits may be readily detected by autoradiography after gel electrophoresis. One skilled in the art will recognize that other methods of labeling and detection may be used alternatively.

In alternative in vitro assay is designed to measure cleavage of a caspase substrate analog (e.g., Acetyl-DEVD-aminomethylcoumarin (amc), lamin, poly-(ADP-ribose) polymerase (PARP), and the like, a variety of which are commercially available). Substrate turnover (e.g., substrate hydrolysis) may be assayed using either comparison of timecourse (i e., progress curve) assays (e.g., evolution of activity and substrate hydrolysis rate analysis via steady-state rate comparison) or endpoint analysis (e.g., final fluorescence minus initial fluorescence). Briefly, in this assay the membrane fraction is incubated with a candidate agent along with the caspase substrate. Detection of cleaved substrate is performed by any one of a variety of standard methods. Generally, the substrate will be labeled and followed by an appropriate detection means.

Typical substrates utilized within the context of the present invention include those agents whose turnover measures, directly or indirectly, the apoptotic pathway and, in particular, the enzymatic activity of one or more caspase molecules. In this regard a variety of substrates such as labeled caspase molecules, lamin, PARP and caspase substrate analogues are known by those of skill in the art. Such substrates are also available commercially from such companies as Oncogene Research Products, Cambridge, Mass. Illustrative substrate analogues which are tagged with fluorescent markers include, ZEVD-amc (carbobenzoxy-Glu-Val-Asp-aminomethylcoumarin), YVAD-amc (Acetyl-Tyr-Val-Ala-Asp-aminomethylcoumarin; SEQ ID NO:7), and DEVD-amc (Acetyl-Asp-Glu-Val-Asp-aminomethylcoumarin; SEQ ID NO:6). In a preferred embodiment, the caspase substrate comprises a site cleaved by a caspase selected from the group consisting of a protein, a polypeptide, an oligopeptide, a peptide mimetic and a peptide.

Moreover, any known enzymatic analysis can be used to follow the inhibitory or enhancing ability of a candidate agent with regard to membrane derived caspase-3 activity. It would be apparent to one of ordinary skill in the art that the candidate agent (i.e., inhibitor or enhancer) may be incubated with the cell prior to fractionation or with the membrane fraction after fractionation, but prior to detection. Moreover, the candidate agent may be contacted or contacted and incubated with the membrane fraction concurrently with a caspase substrate.

The assays briefly described herein may be used to identify an enhancer or inhibitor that specifically affects membrane derived caspase activity. A variety of methodologies exist that can be used to investigate the effect of a candidate compound. Such methodologies are those commonly used to analyze enzymatic reactions and include, for example, SDS-PAGE, spectroscopy, HPLC analysis, autoradiography, chemiluminescence, chromogenic reactions, and immunochemistry (e.g. blotting, precipitating, etc.).

In an additional embodiment, compositions of membrane derived caspase-3 nucleic acid molecules or polypeptides may be administered either alone or as a pharmaceutical composition. These compositions may contain any of the above described inhibitors, enhancers, DNA molecules, vectors or host cells, along with a pharmaceutically or physiologically acceptable carrier, excipient or diluent. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

Compositions of the present invention may be formulated for the manner of administration indicated, including for example, for oral, nasal, venous, intracranial, intraperitoneal, subcutaneous, or intramuscular administration. In a particularly preferred embodiment, a nucleic acid expression vector or gene delivery vehicle may be delivered by administering the composition to the circulatory system of a mammal in which a suitable cell is located. Within other embodiments of the invention, the compositions described herein may be administered as part of a sustained release implant. Within yet other embodiments, compositions of the present invention may be formulized as a lyophilizate, utilizing appropriate excipients which provide stability as a lyophilizate, and subsequent to rehydration. One skilled in the art may further formulate the enhancers or inhibitors of this invention in an appropriate manner, and in accordance with accepted practices, such as those disclosed in Remington's Pharmaceutical Sciences, Gennaro, Ed., Mack Publishing Co., Easton, Pa. 1990. Pharmaceutical compositions are useful for both diagnostic or therapeutic purposes.

Pharmaceutical compositions of the present invention may be administered in a manner appropriate to the disease to be treated (or prevented). The quantity and frequency of administration will be determined by such factors as the condition of the patient, and the type and severity of the patient's disease. Dosages may be determined most accurately during clinical trials. Patients may be monitored for therapeutic effectiveness by appropriate technology, including signs of clinical exacerbation, imaging and the like.

The following examples are offered by way of illustration, and not by way of limitation.

EXAMPLES

Example 1

Cell-Lines and Cell Culture 697 human lymphoblastoid cells stably infected with a retroviral expression construct containing Bcl-2 cDNA (697-Bcl-2 cells) or a control neomycin resistance gene (697-neo-cells) (Miyashita and Reed, Blood 81:151, 1993) (obtained from Dr. John Reed, Burnham Institute) were used in these studies. The cells were maintained in mid-log phase growth in RPMI 1640 medium (Irvine Scientific, Santa Ana, Calif.) supplemented with 10% fetal bovine serum ((FBS) Hyclone, Logan, Utah), 0.2 mg/ml G-418 (Gibco, Gaithersburg, Md.) and 0.1 mg/ml penicillin/streptomycin (Irvine Scientific). Murine dopaminergic MN9D cells (obtained from Dr. A. Heller, University of Chicago) were grown in DMEM medium (Irvine Scientific) supplemented with 10% FBS, 2 mM glutamine and 0.1 mg/ml penicillin/streptomycin. Mouse brain cortical cells were prepared at E15 of gestation in Hank's buffered saline solution (Irvine Scientific) with 15 mM HEPES. The tissue was briefly dissociated with 0.1% trypsin and washed thoroughly with MEM medium supplemented with 10% FBS and 0.4 mg/ml DNase I (Sigma, St. Louis, Mo.), gently triturated and flash frozen.

Example 2

Sub-Cellular Fractionation

Frozen cell pellets containing $\approx 10^9$ cells were thawed and resuspended in cold hypotonic buffer (10 mM Na-HEPES, 5 mM $MgCl_2$, 42 mM KCl, pH 7.4) supplemented with 1 mM PMSF, 1 µg/ml leupeptin, 1 µg/ml pepstatin A, 5 µg/ml aprotinin, 0.1 mM EDTA, 0.1 mM EGTA and 5 mM DTT (Sigma) to a density of $\approx 1.5 \times 10^8$ cells/ml. The samples were incubated on ice for 30 min at which time the cells were lysed using 30–40 strokes with a Dounce homogenizer. The sample was centrifuged twice for 10 min at 500×g, 4° C. to separate the nuclei. The nuclear pellets were then washed twice in the same buffer supplemented with 1.6M sucrose, yielding the nuclear fraction. The supernatant was then centrifuged at 14,000×g for 30 min at 4° C. to pellet the heavy membranes. The heavy membranes were washed 3 times with 1.5 ml cold hypotonic buffer containing protease inhibitors and DTT. The washed membranes were resuspended in hypotonic buffer so that the total protein concentration was approximately 2 mg/ml, yielding the heavy membrane fraction, that was either flash frozen or used immediately for enzymatic measurements without freezing. The 14,000×g supernatant was centrifuged at 100,000×g for 30 min at 4° C., yielding a supernatant (cytoplasmic fraction) and a pellet (light membrane fraction). Protein concentrations were measured using Protein Assay Kit II from BioRad with bovine serum albumin as the calibration standard. In some experiments, cell pellets were lysed as above, but without a freezing step. To test effects of cytochrome c on caspase activity, some samples were treated with 10 µg/ml bovine cytochrome c (Sigma Chemical, St. Louis, Mo.) throughout the entire isolation procedure. In some experiments, mitochondrial fractions were prepared from lysed 697-neo and 697-Bcl-2 cells by the rat liver mitochondrial methods of Mancini and collaborators (Mancini et al. J. Cell Biol 140:1485, 1998) and used without freezing.

Example 3

Immunoblotting and N-Terminal Sequence Analysis

Subcellular fractions (50 µg protein per lane) were resolved by SDS-PAGE on 12% or 16% gels (Novex, La Jolla, Calif.) and transferred to Immobilon PVDF membranes (Millipore, Bedford, Mass.). Membranes were blocked in PBS/0.1% Tween 20 (PBST)+0.4% casein (I-block, Tropix, Bedford, Mass.). Blots were incubated in 1 µg/ml primary antibody diluted in PBST/casein for 1 hour. Following three washes in PBST, blots were incubated for one hour in 1:15,000 dilutions of alkaline phosphatase conjugated goat antirabbit IgG or goat anti-mouse IgG (Tropix) in PBST/casein. Blots were then washed twice with PBST, twice in assay buffer (10 mM diethanolamine, pH 10.0, 1 mM $MgCl_2$) and then incubated in 250 µM chemiluminescent substrate CSPD (Tropix) in assay buffer and exposed to Biomax film (Kodak, Rochester, N.Y.) overnight.

In some cases, following the secondary antibody incubations, the blots were washed with 10 mM Tris, pH9.5, 1 mM $MgCl_2$. The blots were then incubated for 30 minutes in 1.25 µg/ml DDAO phosphate (Amersham, Arlington Heights, Ill.) dissolved in the Tris buffer. The blots were scanned using the STORM fluorescence imager (Molecular Dynamics, Sunnyvale, Calif.). The antibodies used were against Bcl-2 (Transduction Labs, Lexington, Ky.), caspase-3 (Srinivasan et al., Cell Death Differ. 12:1004, 1998), cytochrome c (Pharmingen, San Diego, Calif.), cytochrome oxidase, subunit IV (Molecular Probes, Portland, Oreg.), D4-GDP dissociation inhibitor (D4-GDI) (a gift of Dr. G. Bokoch, Scripps Research Institute, La Jolla, Calif.) and poly(ADP-ribose) polymerase (PARP) (Enzyme Systems, Livermore, Calif.).

For N-terminal sequencing analysis, the caspase bands were transferred to PVDF, visualized using Coomassie R-250 stain, dried and then excised. The PVDF bound band was then analyzed by N-terminal microsequence analysis.

Example 4

Activity Assays

Caspase activity was measured by mixing 50 µl of an enzyme-containing fraction and 200 µl of 25 µM DEVD-amc (Asp-Glu-Val-Asp-aminomethylcoumarin; SEQ ID NO:6) substrate in ICE buffer (20 mM HEPES, 1 mM EDTA, 0.1% CHAPS, 10% sucrose, 5 mM DTT, pH 7.5) in duplicate Cytoplate wells. Product formation was monitored by the increase in fluorescence (ex=360 nm, em=460 nm) over 1–2 hours at 30° C. using the CytoFluor 4000 plate reader (Perseptive Biosystems, Framingham, Mass.). For kinetic studies, the substrate concentration was varied in the range 1–200 µM. $K_M$ values were calculated from these measurements using the equation:

$$\Delta FL/\Delta t = (\Delta FL/\Delta t)_{MAX}/(1+K_M/[S])$$

where ΔFL/Δt is the observed initial rate of fluorescence change at substrate concentration [S] and $(\Delta FL/\Delta t)_{MAX}$ is the initial rate of fluorescence change at saturating substrate concentrations. For inhibition studies, 50 µl of the enzyme was pretreated with 150 µl inhibitor for 30 min at room temperature prior to the addition of 50 µl of 50 µM substrate solution. Inhibitor $IC_{50}$ values were determined using the equation:

$$\Delta FL/\Delta t = (\Delta FL/\Delta t)_o/(1+[I]/IC_{50})$$

ΔFL/Δt is the observed initial rate of fluorescence change at inhibitor concentration [I] and $(\Delta FL/\Delta t)_o$ is the initial rate fluorescence change for the uninhibited enzyme.

Example 5

Activation Assays

Heavy membrane samples were diluted to 1 mg/ml in hypotonic buffer or in 0.25 M sucrose, 10 mM MOPS, 2 mM EDTA, pH 7.4 (Mancini, et al., 1998) containing 5 mM DTT with or without 1% NP-40. Caspase activation was induced by adding 60–160 ng/ml recombinant murine caspase-1 (in bacterial lysate), 2 µg/ml of purified human granzyme B (Enzyme Systems Products, Livermore, Calif.) or buffer, and incubating the samples for 60 min at 30° C. or 37° C. After the activation period, the heavy membrane pellet was removed from the sample by centrifugation for 10 min at 14,000×g at 4° C. In all experiments, the observed DEVD-AMC cleaving activities in the supernatants were corrected for the activity of the exogenous caspase-1, which was negligible as compared to the total activity. In some experiments, caspase-1 activity was rapidly quenched at specific time points by the addition of one-tenth volume 3 µM YVADaldehyde (Bachem Bioscience, King of Prussia, Pa.) prior to centrifugation. To examine the time course of spontaneous activation of caspase activity from membranes, 50 µl of heavy membrane slurry containing 50–100 µg total protein was mixed with 200 µl hypotonic buffer containing 25 µM DEVD-amc substrate and 6 mM DTT in 96 well Cytofluor plates and fluorescence was measured over time. At selected time points, aliquots were removed from some wells, centrifuged for 10 min at 14,000×g to remove the heavy membranes and the supernatant was added back into the 96 well plate to measure the soluble DEVD-amc cleavage activity. In some experiments, subcellular fractions were treated with 1 µg/ml bovine cytochrome c (Sigma) and 50 µM dATP (New England Biolabs, Beverly, Mass.) (final concentrations) for 40 min at 30° C. prior to measurement of caspase activity.

Example 6

Recombinant Caspase and P53 Production

BL21 (DE3) cells harboring a plasmid containing the cloned human caspase-3 cDNA (Fernandes-Alnemri et al., *J. Biol. Chem.* 269:30761, 1994) (provided by Dr. E. Alnemri, Thomas Jefferson University) ligated into the Bam HI/Xho I sites of pET21b (Novagen, Madison, Wis.) and were grown in one liter LB medium containing 0.1 mg/ml ampicillin at 37° C. When the culture density reached $A_{600}$=1, IPTG (Sigma) was added to a concentration of 1 mM and the culture was incubated at 25° C. for three hours. The cells were harvested by centrifugation at 2,000×g for 15 min at 4° C. The cells were lysed using one freeze-thaw cycle in 100 ml Binding buffer (20 mM TrisCl, 500 mM NaCl, 5 mM imidazole, 0.1% triton X-100) with 0.1 mg/ml lysozyme. Cell debris was removed from the sample by centrifugation at 20,000×g, for 30 min at 4° C. The lysed cells were treated just prior to centrifugation with $MgCl_2$ and DNase I to reduce viscosity. The supernatant was filtered through a 0.45 µm syringe filter and loaded onto a 1 ml $Ni+^2$—charged HiTrap Chelating column (Amersham Pharmacia, Uppsala, Sweden) at a 1 ml/min flow rate. The column was washed at 1 ml/min with 10 ml Binding buffer followed by 10 ml Binding Buffer containing 60 mM imidazole. The caspase-3 protein was eluted from the column using a 30 ml linear gradient of imidazole (60–500 mM). Protein p35 (early p35 protein from *Autographa californica* nuclear polyhedrosis virus, Clem et al., Science 254:1388, 1992) was produced and purified using an identical procedure.

Recombinant murine caspase-1 was expressed using BL21 (DE3) pLys S cells harboring pET3ap30mICEFLAG plasmid (a generous gift of Drs. H. R. Horvitz and Ding Xue, MIT) which contains the p30 caspase-1 cDNA inserted into the Nde I/BamH I sites of the pET3a expression vector (Novagen). A three liter culture was grown at 37° C. in Induction medium (20 g/l tryptone, 10 g/l yeast extract, 6 g/l NaCl, 3 g/l $Na_2HPO_4$, 1 g/l $KH_2PO_4$, 1 mM $MgCl_2$, 0.1 mM $CaCl_2$, pH 7.4) containing 0.1 mg/ml ampicillin and 0.025 mg/ml chloramphenicol. When the culture reached a density of $A_{600}$=1.0, IPTG was added to 1 mM and the culture was shaken at 25° C. for 3 hours. The cells were collected by centrifugation at 2000×g for 15 min at 4° C. and resuspended in 100 ml cold buffer containing 25 mM TrisCl, pH 8.0, 25 mM KCl, 0.1% triton X-100, and 0.1 mg/ml lysozyme (InovaTech, Abbottsford, B.C., Canada). The cells were lysed using one freeze/thaw cycle and lysate was clarified by treating the sample with 0.02 mg/ml DNase I, 0.5 mM $MgCl_2$ (Sigma) for 60 min and then centrifuging at 20,000×g for 30 min at 4° C. to remove cell debris.

Example 7

Affinity Purification of Membrane Derived Caspase-3

Heavy membranes were prepared from frozen 697 cell pellets containing ≈$10^{12}$ cells total as described in Example 2. The heavy membranes were resuspended in hypotonic buffer (to a density of ≈$10^9$ cells/ml) and activated with recombinant caspase-1 for 90 min at 30° C. The activation of the membrane derived procaspase-3 with recombinant caspase-1 is necessary prior to purification since procaspase-3 does not bind the DEVDaldehyde affinity reagent effectively. Supernatant from activated heavy membranes was treated with 300 nM YVADaldehyde for 15 min such that caspase-1 activity is completely inhibited. The resultant sample was filtered through a 0.45 µm acrodisc syringe filter, and subsequently loaded at 1 mL/min onto a 0.8 ml streptavidin agarose (Sigma, St. Louis, Mo.) column charged with biotinyl-DEVDaldehyde affinity reagent (Peptides International, Louisville, Ky.). The column was washed three times with 12-mL hypotonic buffer supplemented with 0.15 M NaCl to remove nonspecifically bound material. After the resin was washed with 3 mL hypotonic buffer, the resin was resuspended with 0.45 ml additional hypotonic buffer and split into two portions. Protein was eluted from the larger portion (0.65 mL) under denaturing conditions by treating the resin with 0.6 mL 0.4% SDS in 20 mM MES buffer, pH 5.5 for 15 min at 65° C. After elution the sample was lyophilized prior to SDS-PAGE analysis. The smaller portion (0.15 mL resin) was treated with 2 mL of 100 mM hydroxylamine, 20 mM oxidized glutathione, pH 7.5 for 8 hours to elute the caspase under nondenaturing conditions (Thornberry, et al., *Nature* 396:768, 1992). After elution the hydroxylamine/glutathione was removed by passing the sample through a PD 10 desalting column (Amersham-Pharmacia) equilibrated with ICE buffer+50 mM NaCl. The caspase was then rapidly reactivated by dilution in buffer containing 30 mM DTT.

Figures 5A, 5B:
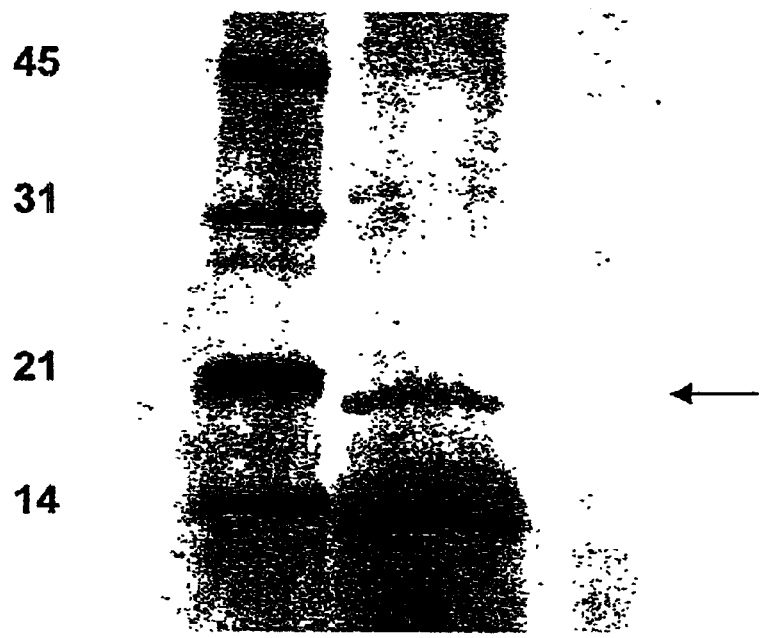
FIG. 5A is a scanned image of affinity-purified membrane derived caspase-3 analyzed by SDS-PAGE and visualized with Coomassie stain. The position of the 19 kDa large subunit is indicated by the arrow and the molecular weights (kDa) of each of the molecular weight markers are indicated.
FIG. 5B illustrates the N-terminal sequence of human caspase-3 protein (SEQ ID NO:4) wherein residues 14–23 of cytoplasmic caspase-3 are identical to the observed N-terminal sequence of the 19 kDa band of the membrane derived caspase (underlined). The procaspase-3 aspartic acid cleavage sites are in boldface type. The N-terminal residues of 697 cell cytoplasmic and recombinant bacterially expressed caspase-3 (Ser 10 and Ser 29, respectively) are indicated with arrows.

SDS-PAGE-analysis of the denatured affinity purified caspase indicates that the heavy membrane caspase is comprised of a large 19-kDa subunit and a smaller 12-kDa subunit (FIG. 5A). The N-terminal sequence of the first 10 residues of the 19-kDa subunit is identical to the sequence of residues 14–23 of human caspase-3 (FIG. 5B). The apparent cleavage after Ile 13 was unexpected because cytoplasmic procaspase-3 is known to be processed after Asp 9 and Asp 28 in other cell systems (Nicholson et al., 1995; Faleiro et al., 1997). It was further observed that the N-terminus of the large subunits of cytoplasmic caspase-3 from 697 cells (activated with caspase-1) and bacterially-expressed recombinant caspase-3 are Ser 10 and Ser 29, respectively (data not shown).

Example 8

Characterization of Subcellular Fractions

Subcellular fractions were prepared from 697 cells stably infected with retroviral constructs expressing either Bcl-2 cDNA or a neomycin resistance gene (697-Bcl-2 and 697-neo cells, respectively) (Miyashita and Reed, *Blood* 81:151, 1993). Nuclear, heavy membrane, light membrane, and cytosolic fractions were isolated from these cells, and characterized by Western blot analysis with antibodies specific for proteins with distinct known subcellular distributions, as in Example 3. Antibodies used were directed against cytochrome oxidase, specific for mitochondrial inner membrane (Tzagoloff, *Cell* 91:627, 1982), poly(ADP-ribose) polymerase (PARP), specific for nuclei (Berger, *Radiat Res* 101:4, 1985), D4-GDP dissociation inhibitor (D4-GDI), specific for cytoplasm (Na et al., *J. Biol Chem* 271:11209, 1996) and Bcl-2. The immunoblots were visualized on film by chemiluminescense, except the cytochrome oxidase immunoblot which was visualized by chemifluorescence.

Figure 7:
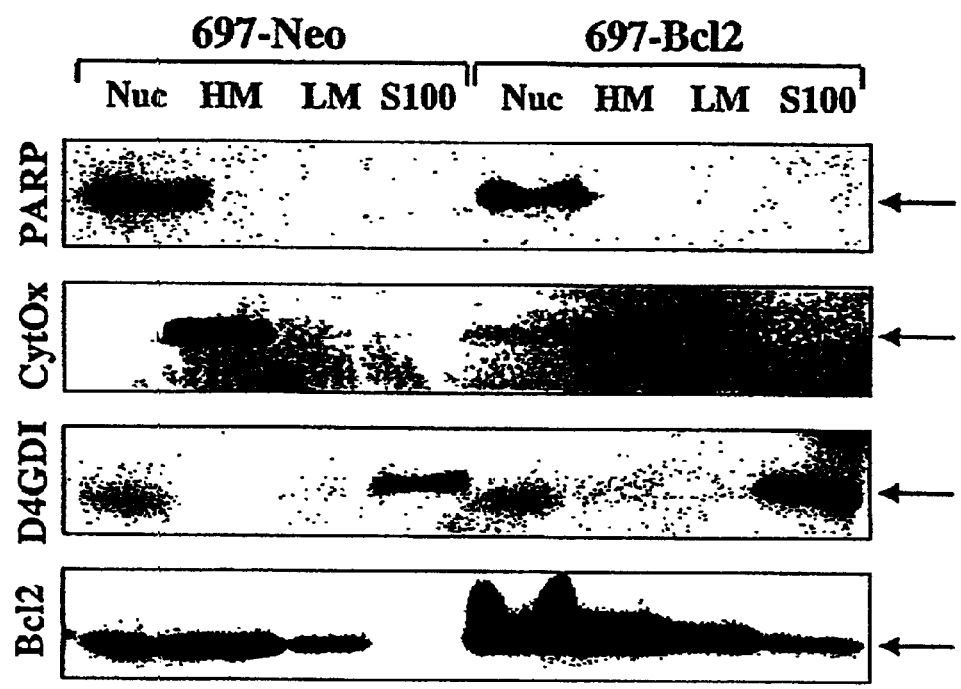
FIG. 7 is a scanned image of an immunoblot representing SDS-PAGE analysis of subcellular fractions from 697-neo and 697-Bcl-2 cells using antibodies to PARP, cytochrome oxidase (subunit IV), D4GDI and Bcl-2. Nuc=nuclear fraction, HM=heavy membrane fraction, LM=light membrane fraction, S100=cytosolic fraction. Arrows indicate the specific immunoreactive band.

As shown in FIG. 7, the mitochondrial marker was found almost exclusively in the heavy membrane fraction, the nuclear marker only in the nuclear fraction, and the cytoplasmic marker only in the cytoplasmic fraction. Thus, the fractionation methods employed generated fractions with the expected subcellular distribution of marker proteins. Importantly, cytoplasmic contamination of the nuclear and membrane fractions could not be detected, and only minimal mitochondrial contamination of nuclear fractions was detected (the diffuse D4-GDI reactive band in the nuclear fraction shown in FIG. 7 is non-specific). Western analysis of fractions from 697-neo cells with an antibody to human Bcl-2 (FIG. 7) demonstrated strong reactivity in nuclear and heavy membrane fractions, weaker reactivity in the light membrane fraction, and undetectable signal in cytoplasm, in accord with previous results (Krajewski et al., 1993; Yang et al., 1995; Lithgow et al., *Cell Growth Differ* 3:411, 1994). Similar analysis of fractions from 697-Bcl-2 cells showed significant overexpression.

Example 9

Subcellular Distribution of Cleavage Activity

Figures 8A, 8B, 8C, 8D:
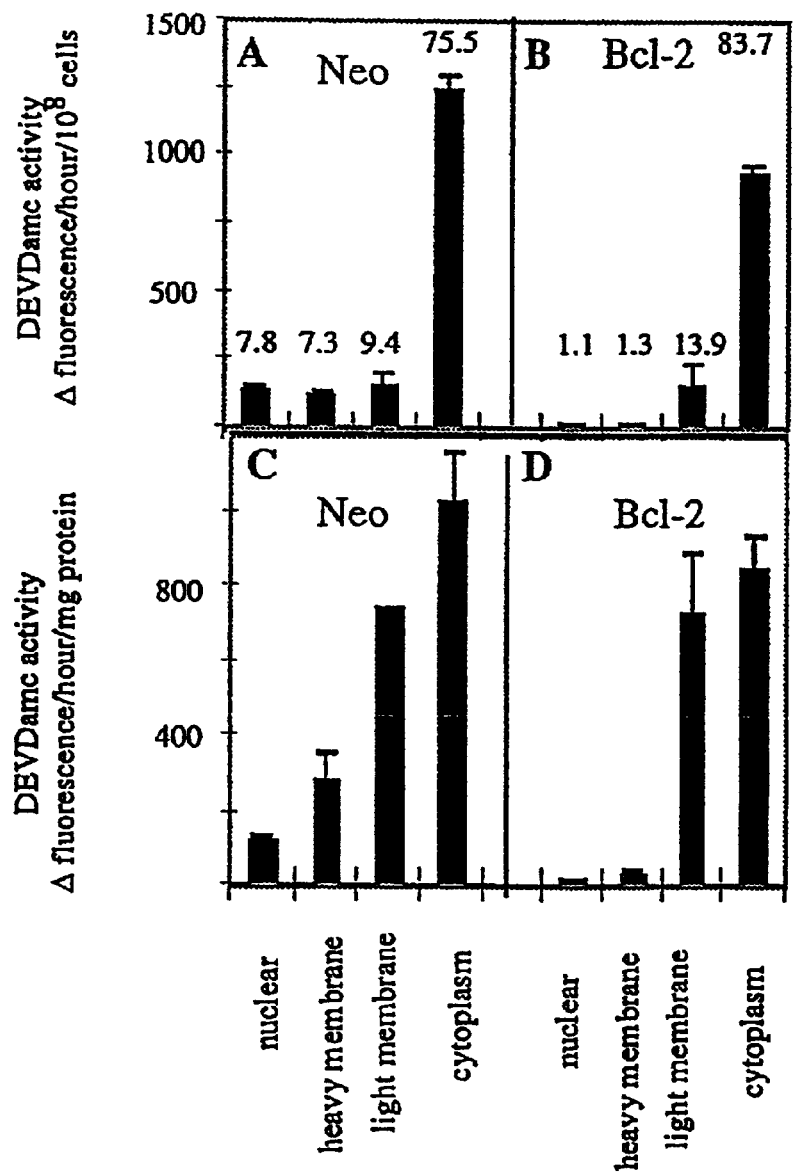
FIGS. 8A–D are histograms of caspase substrate cleavage activity in subcellular fractions.

Preliminary experiments indicated that caspase activity was associated with membranes derived from unstimulated cells. To determine the subcellular distribution of such caspases, caspase activity in the subcellular fractions from 697-neo cells was quantitated by incubating these cells with the substrate DEVD-amc, and measuring the increase in fluorescence over the subsequent 2 hours. DEVD-amc is a useful substrate for all caspases characterized to date, with the exception of caspase-2 and caspase-14 (Talanian et al., *J. Biol. Chem.* 272:9677, 1997; and data not shown). While most of the DEVD-amc cleavage activity (~75%) was in the cytoplasmic fraction, a substantial amount of the cleavage activity was found in the nuclear, heavy membrane and light membrane fractions (FIGS. 8A and 8C). DEVD-amc cleavage activity in subcellular fractions of 697 cells transfected with neo control or Bcl-2 expression vectors were fractionated and the caspase activity of each subcellular fraction was assayed. The observed cleavage activity values in the histogram are normalized for constant number of cells (FIGS. 8A–8B) or mg protein (FIGS. 8C–8D). The values listed for each column in A and B indicate the percent of total cleavage activity present in each fraction. The error bars in FIGS. 8A–8D indicate the range of observed values for two independent 697 cell preparations.

The major DEVD-amc cleaving activity in each fraction was indeed caspase activity since it was potently blocked by specific caspase inhibitors (Table II, column 1 of Example 14, and data not shown).

Example 10

Extraction of Membrane Derived Procaspase-3 with Detergent

Figure 4:
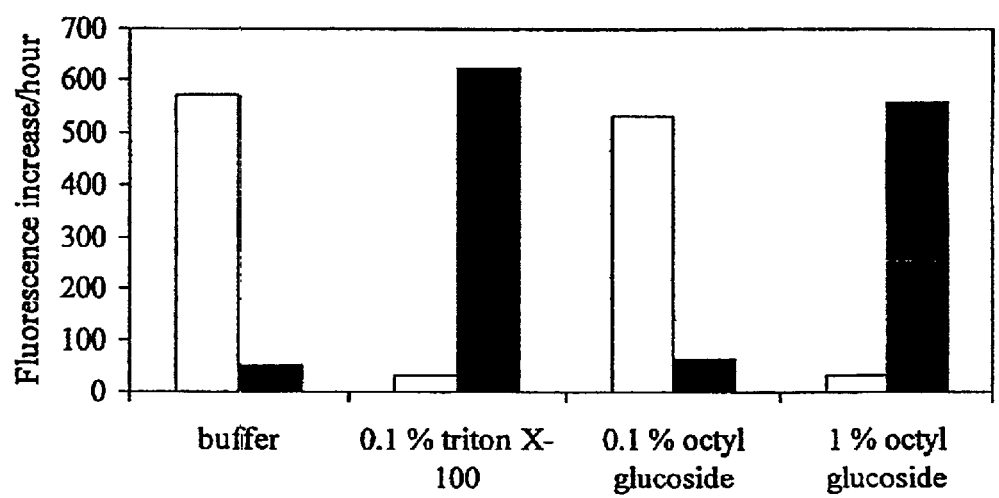
FIG. 4 is a graph illustrating that membrane derived procaspase-3 is tightly associated to heavy membranes and can be extracted with detergents.

The membrane derived procaspase-3 is tightly associated with membranes and the protein/membrane interaction can withstand extensive buffer washes and freeze/thaw cycles (unpublished data). Therefore effects of detergent on the membrane procaspase using nonionic and zwitterionic detergents were determined. The membrane fractions were treated with detergents for 30 min on ice and then the insoluble pellet was removed by centrifugation. The localization of the procaspase was determined by treating the supernatant and pellet fractions with caspase-1 and measuring the DEVD-AMC hydrolysis activity in each fraction (FIG. 4). As noted in Example 5, caspase-1 activity was rapidly quenched at specific time points by the addition of one-tenth volume 3 μM YVADaldehyde prior to centrifugation in some experiments. Treatment of the membranes with either 0.1% triton x-100 or 1% β-octyl glucoside efficiently extracted the procaspase from the membrane as indicated by the presence of caspase-1 activatable DEVD-AMC cleavage activity in the supernatant, but not the membrane pellet. As expected, caspase-1-activatable DEVD-AMC cleavage activity remained associated with the membrane pellet in control buffer treated samples (FIG. 4). Caspase-1 treatment is necessary for activation of the detergent solubilized procaspase since no significant DEVD-AMC cleavage activity was detected in samples not treated with caspase-1 (data not shown). This result indicates that solubilized procaspase does not spontaneously activate. Procaspase could not be extracted from the membranes when they were treated with 0.1% β-octyl glucoside, which is a concentration below the critical micelle concentration (CMC) for this detergent (0.7%). This result suggests that detergent micelle formation is required for membrane derived procaspase-3 solubilization. Very similar results were observed for CHAPS, a zwitterionic detergent with a CMC similar to that of β-octyl glucoside (data not shown).

Example 11

BCL-2 Suppression of Membrane-Derived Caspase Activity

The effect of Bcl-2 on the caspase activities in the various subcellular fractions was also investigated. When subcellular fractions derived from 697-Bcl-2 cells were prepared and incubated with DEVD-amc substrate, substantially reduced caspase activity was observed in the nuclear and heavy membrane fractions compared with 697-neo cells (FIG. 8B). This Bcl-2 effect was evident when the caspase activity was measured on a per cell basis or per mg protein and resulted in an 80–90% reduction in caspase activity in these fractions (FIGS. 8B and 8D). The effect of Bcl-2 expression on caspase activity in these fractions was specific, since little if any suppression was seen in the activities observed in the cytoplasmic or light membrane fractions (FIGS. 8A–8D). These observations suggest that the membrane-derived caspase activity is not simply from a small percentage of apoptotic cells in the 697-neo cultures whose numbers were suppressed in the 697-Bcl-2 cultures. If that were the case, one would also expect to see major differences in caspase activities between cytoplasmic fractions derived from 697-neo compared to 697-Bcl-2 cells. Indeed, control experiments demonstrated that when 697-neo cells were induced to undergo apoptosis by staurosporine treatment, the major increase in caspase activity was found in the cytoplasm (data not shown).

The ability of Bcl-2 to suppress membrane-derived caspase activity was not limited to the 697 lymphoblastoid cells, since similar effects were observed in Jurkat T cells and FL5.12 cells (data not shown). Since the present data, as well as other published studies, have demonstrated that Bcl-2 protein is found predominantly in nuclear envelope and heavy membrane fractions (FIG. 7; Krajewski et al., 1993; Yang et al., 1995), the present results were compatible with the possibility that Bcl-2 might act locally to regulate this membrane-derived caspase activity. In an effort to begin analyzing such mechanisms, this membrane-derived, Bcl-2suppressible caspase activity was further characterized.

Example 12

Figure 9A:
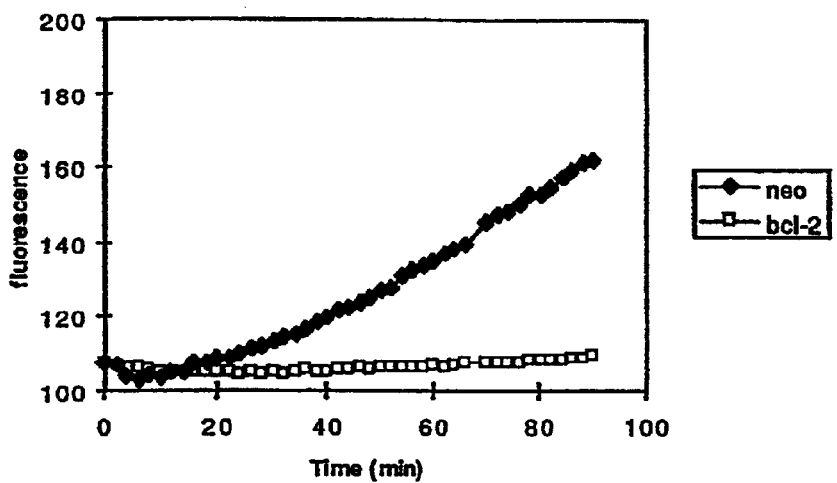
FIGS. 9A and 9B are graphs representing membrane-associated procaspase-3 spontaneous activation.
Figure 9B:
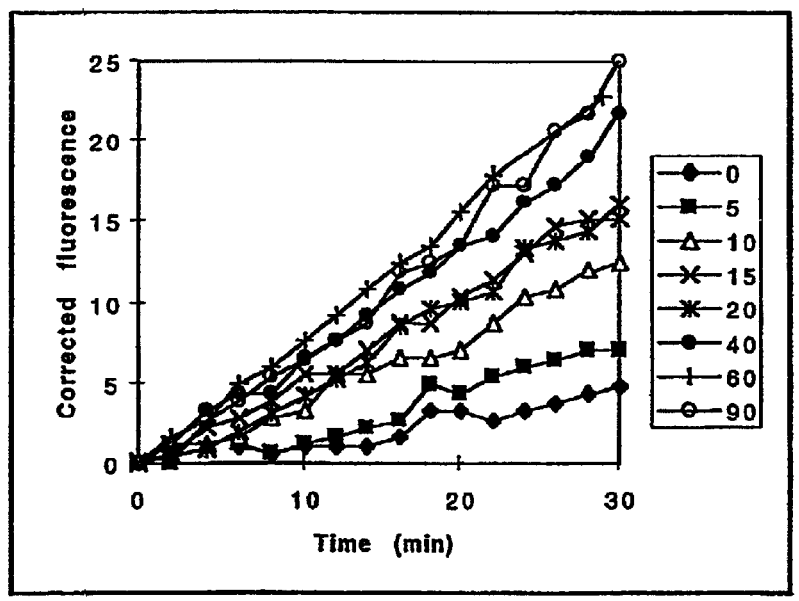

Spontaneous Activation and Membrane Release of Membrane Derived Caspase Activity It was possible that the membrane derived caspase activity was due either to an active membrane-bound enzyme, or alternatively, to the spontaneous activation and release of a soluble active enzyme. Therefore a set of experiments was designed to distinguish between these two possibilities. First, to freshly prepared heavy membranes derived from 697-neo cells (neo-membranes), hypotonic buffer and DEVD-amc substrate at room temperature was immediately added, and the emergence of amc fluorescence over a 90 minute period was measured (FIG. 9A). The DEVD-amc cleavage activity of was measured by adding 20 μg of freshly prepared membranes into hypotonic buffer containing 20 μM DEVD-amc (final concentration). The evolution of amc product was measured by the change in fluorescence (ex=360 nm, em=460 nm) at room temperature. The data demonstrate that there is little detectable fluorescence change over the first 15 minutes of incubation, but after this lag period, the rate of amc production increases markedly (FIG. 9A). These results indicate that the freshly prepared membranes do not contain active caspase, but that activation occurred spontaneously during the incubation period. To assess whether this newly activated caspase was soluble or membrane bound, membranes were incubated for different periods of time (0 to 90 minutes), following which the samples were centrifuged for 10 minutes at 14,000×g at 10° C. and the resulting supernatants were assayed for caspase activity with DEVD-amc substrate. These data demonstrated that very little caspase activity was present in the supernatant initially, but that soluble caspase activity appeared thereafter (FIG. 9B). Quantitative analysis of these data demonstrated that for each supernatant, fluorescence increased linearly, indicating that once released from the membranes, no further activation occurred. Furthermore, the slopes of these curves (FIG. 9B) approximate the instantaneous slopes of the corresponding time points in the progress curve for the heavy membrane slurry (FIG. 9A). Therefore, all of the caspase-3 activity can be accounted for in the supernatant fraction, indicating that all active enzyme had been released from the membranes. In contrast to the neo-membranes, membranes derived from the 697-Bcl-2 cells (Bcl-2-membranes) failed to generate significant DEVD-amc cleaving activity (FIG. 9A).

Example 13

Procaspase-3 Presence in Heavy Membranes and Activation Therefrom

Figure 10:
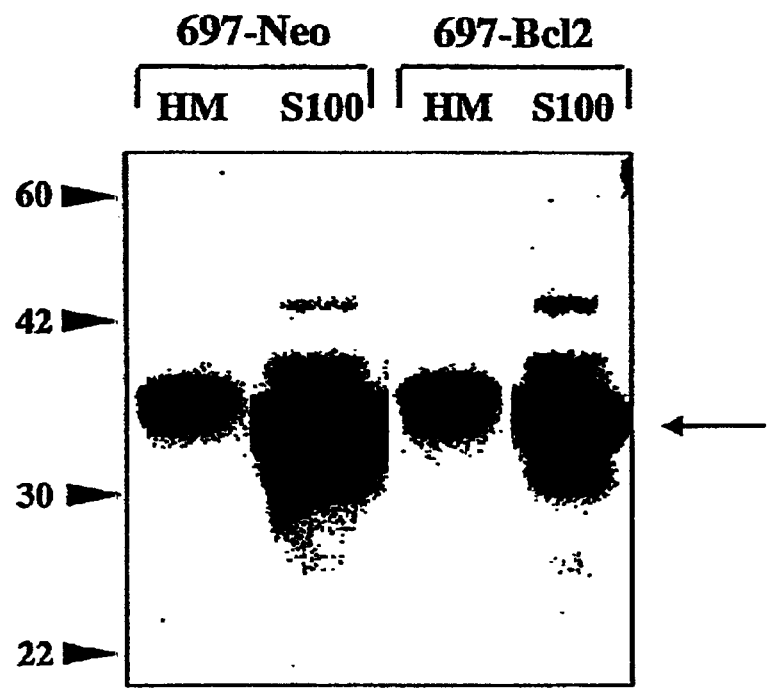
FIG. 10 is a scanned image of an immunoblot representing SDS-PAGE analysis of heavy membrane and cytosolic fractions from 697-neo and 697-Bcl-2 cells, probed with an anti-caspase-3 polyclonal antibody. The arrowheads indicate the migration of protein size markers (Rainbow Markers, Novex); the arrow indicates procaspase-3. HM=heavy membrane fractions; S100=cytosolic fraction.

The lack of DEVD-amc cleaving activity in the Bcl-2-membranes could be due either to the absence of activatable procaspase or suppression of procaspase activation. To distinguish between these alternatives, first, Western blot analysis was performed on the membrane and cytosolic fractions with antibodies specific for caspase-3 (Example 3), since the measured DEVD-amc cleavage activity is in fact due to caspase-3 (see below). The results (FIG. 10) demonstrate the presence of a caspase-3 reactive band that is of similar intensity in both the neo-membranes and Bcl-2-membranes, and that is approximately the size expected for the pro-caspase zymogen. Interestingly, the electrophoretic mobility of the membrane-derived bands was slightly slower than that of cytoplasmic procaspase-3.

Figure 11:
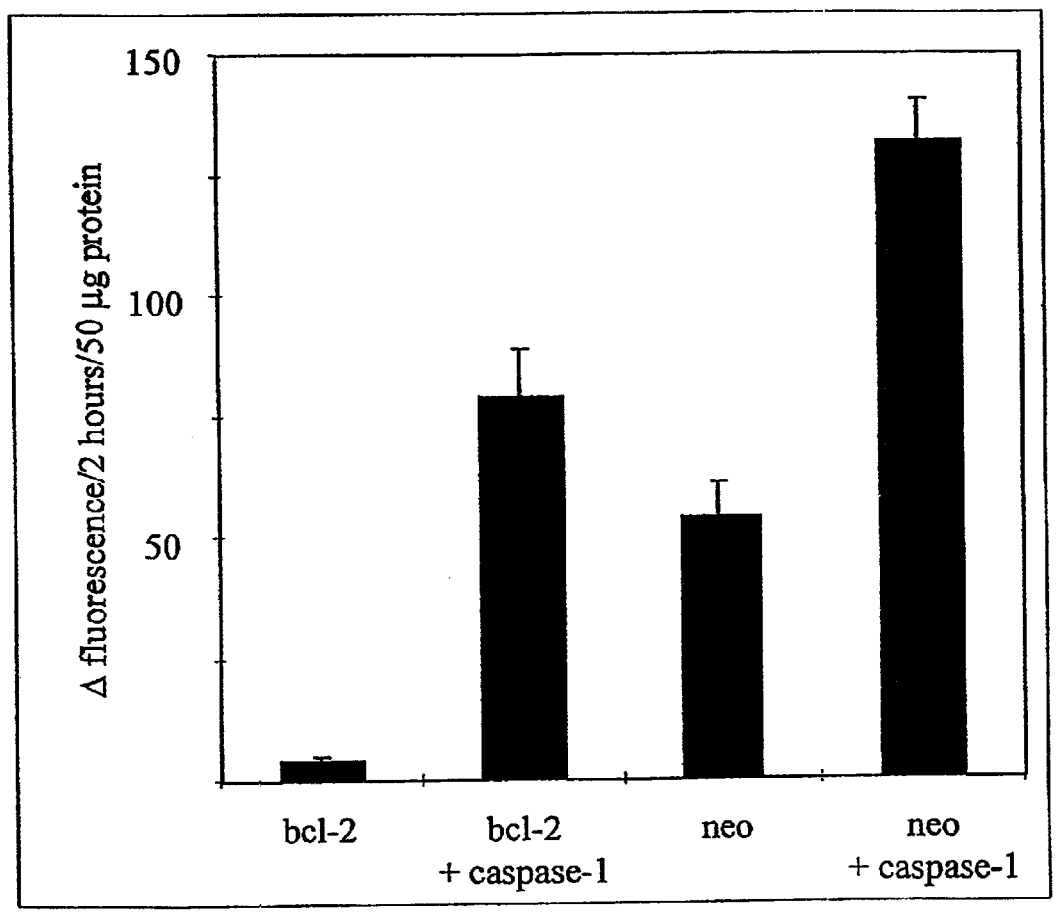
FIG. 11 is a graph illustrating activation of membrane associated DEVD-amc (SEQ ID NO:6) cleavage activity by exogenous caspase-1.

To further demonstrate the presence of procaspase-3 in both neo- and Bcl-2-membranes, activation of these fractions was attempted by treatment with exogenous caspase-1, since procaspases can be activated by proteolytic cleavage at aspartic acid residues between their large and small subunits (Srinivasula et al., *Proc. Natl. Acad. Sci. USA* 93:14486–14491, 1996; Stennicke and Salvesen, *J. Biol. Chem.* 272:25719–25723, 1997; Salvesen and Dixit, *Cell* 91:443–446, 1997). As demonstrated above, membranes derived from Bcl-2 cells showed almost no caspase activity when measured under our standard conditions. However, treatment of the Bcl-2-membranes with caspase-1 caused a robust induction of enzymatic activity (FIG. 11). In this experiment, heavy membrane fractions (containing 50 μg total protein) from 697-Bcl-2 and 697-neo cells were re-suspended and treated with murine caspase-1 for one hour at room temperature. Following centrifugation, the DEVD-amc cleavage activity of the resulting supernatant was measured. The DEVD-amc cleavage activity of caspase-1 treated samples was corrected for exogenous caspase-1 activity by subtracting the fluorescence of control samples containing only caspase-1 from the observed fluorescence. The error bars in FIG. 11 represent the standard deviation of the observed values in 3 independent experiments. The neo-membranes were also activated by exogenous caspase-1. But importantly, following activation, the resulting caspase activities from the Bcl-2- and neo-membranes were always similar, within a factor of two (FIG. 1). Together with the procaspase-3 immunoblot data, this supports the conclusion that comparable levels of procaspase-3 are present in neo- and Bcl-2-membranes.

Figure 2B:
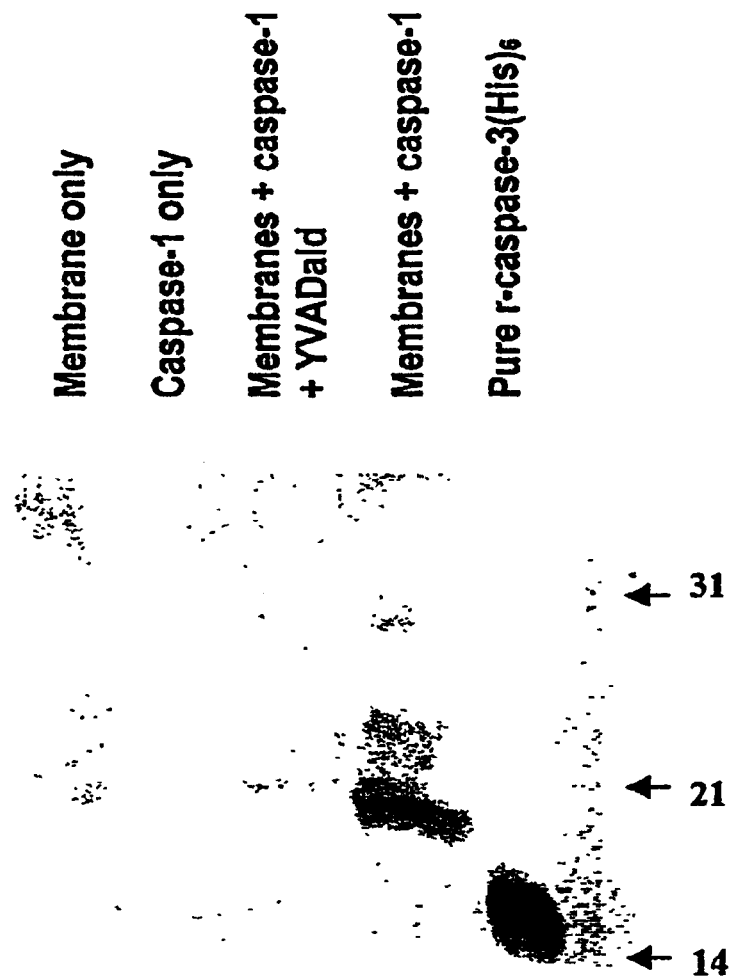
Figure 3:
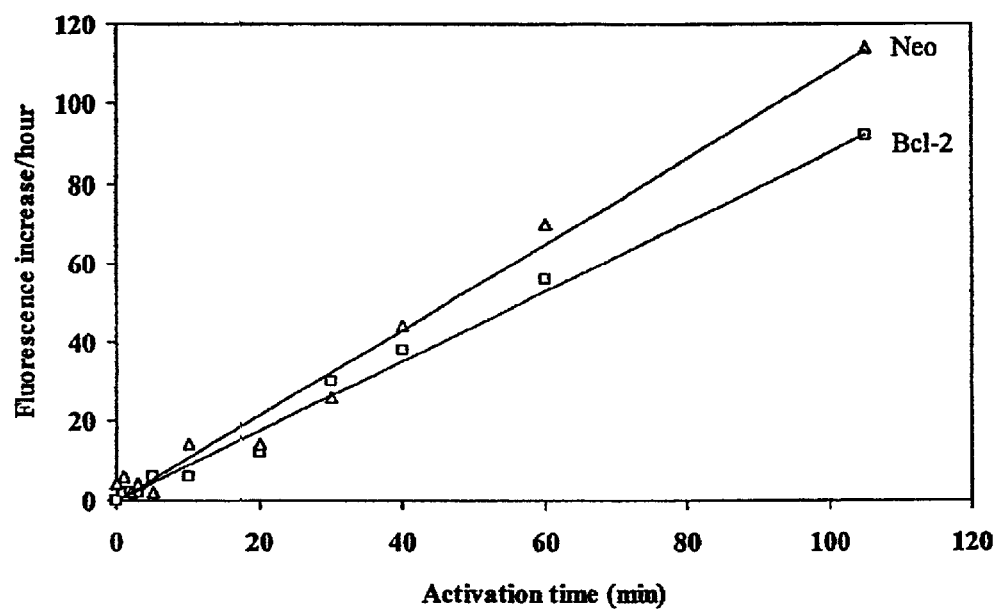
FIG. 3 is a graph illustrating the time course of caspase-1-mediated activation of membrane derived procaspase-3.

Caspase-1 treatment of membranes not only activated the endogenous caspase activity, but also released it from the membranes, since the activity remained in the supernatant when the membranes were removed by centrifugation (FIG. 11). This induction and release were due to the proteolytic activity of caspase-1, since the caspase-1 activation could be completely blocked by 200 nM acYVAD-aldehyde which inhibits caspase-1, but not the membrane caspase, at this concentration (FIG. 2). The time dependence of activation of DEVD-AMC hydrolysis activity in heavy membrane samples by caspase-1 is nearly identical for the neo control and bcl-2 overexpressing cells (FIG. 3). These results indicate that bcl-2 does not block membrane derived procaspase activation by hindering the accessibility of the membrane derived procaspase to activated caspases. The lack of a detectable time lag in the time course plot also indicates that the association between caspase-1 and the membrane derived procaspase occurs rapidly. In addition, these results indicate that both neo- and Bcl-2-expressing cells contain similar amounts of a membrane-derived, inactive procaspase that can be activated by caspase-1. However, without exogenous caspase treatment, only membranes obtained from the neo-expressing cells demonstrated spontaneous membrane derived caspase activation.

In order to characterize the activation and biochemical properties of the membrane caspase, we prepared extensively washed heavy membranes from 697 cells. The isolated membranes contain very little caspase activity (FIG. 2A). Treatment with recombinant caspase-1 causes a rapid, robust activation of the membrane caspase, as indicated by the emergence of DEVD-AMC hydrolysis activity (FIG. 2A). The DEVD-AMC hydrolysis activity does not emanate from caspase-1 as it is not inhibited by 300 nM YVADaldehyde, a potent caspase-1 inhibitor ($IC_{50}$=1 nM). Moreover, caspase-1 catalyzed caspase activation is also detected in immunoblots (FIG. 2B) using an antibody specific for the processed large subunit of caspase-3 (Srinivasan et al., *Cell Death Differ* 12:1004, 1998). Processed caspase-3 is not detected in untreated heavy membrane samples, but a 20 kDa immunoreactive band is readily detected in caspase-1 treated samples (FIG. 2B). A 20-kDa immunoreactive caspase-3 band is often observed in cells induced to undergo apoptosis (Schlegel et al., *J Biol Chem* 271:1841, 1996). The large subunit of purified bacterially expressed caspase-3 migrates as a 17-kDa band (FIG. 2B). The observed difference in the mobility of the large subunits likely reflects differential processing of its N-terminus (Orth et al., *J Biol Chem* 271:20977, 1996; Faleiro et al., *EMBO J* 16:2271, 1997). Pretreatment of caspase-1 with 300 nM YVADaldehyde blocks both the activation of DEVD-AMC hydrolytic activity (FIG. 2A) and the generation of the 20-kDa large subunit (FIG. 2B). At this concentration, YVADaldehyde completely inhibits caspase-1 but not caspase-3 ($IC_{50}$ >10 μM). These results indicate that caspase-1 enzymatic activity is required for membrane procaspase activation.

Example 14

Characterization of Induced and Spontaneous Caspase Activities

The membrane-derived caspase activities were further characterized by measuring the inhibition of DEVD-amc cleavage by several peptide aldehyde inhibitors (Table II). The $IC_{50}$ values for the inhibition of DEVD-amc activity derived from activated Bcl-2-membranes are quite similar to those for the inhibition of the activity derived from neo-membranes, suggesting that caspase-1 activates the same procaspase in both membrane preparations. Furthermore, these $IC_{50}$ values are similar to those for the spontaneously activated DEVD-amc activity derived from neo-membranes, suggesting that the spontaneous and caspase-1-induced activities derive from the same caspase. In all cases, the inhibition data fit well to a simple competitive inhibition curve, suggesting that each DEVD-amc activity arose from a single caspase rather than a mixture of enzymes. The observed $IC_{50}$ values for the membrane derived caspases are very similar to those for purified fully-processed recombinant human caspase-3. Kinetic measurements also indicate that $K_m$ values for hydrolysis of DEVD-amc by the membrane-derived caspases (10 μM) are similar to that observed with fully processed caspase-3 (Nicholson et al., *Nature* 376:37–43, 1995). N-terminal microsequence analysis of activated, affinity purified heavy membrane caspase confirms that this enzyme is indeed human caspase-3.

TABLE II

Heavy membrane (HM) derived caspases from various cell types and recombinant human caspase-3: Inhibition by peptide aldehydes.

| | $IC_{50}$ (nM) | | | | | |
|---|---|---|---|---|---|---|
| inhibitor | 697-neo HM (spontaneous activity) | 697-neo HM (caspase-1 treated) | 697 Bcl-2 HM (caspase-1 treated) | cortical cell HM (caspase-1 treated) | MN9D HM (caspase-1 treated) | r-caspase-3 $(His)_6$ |
| DEVD-ald | 2.3 | 2.8 | 1.3 | 1.0 | 0.72 | 1.0 |
| DFLD-ald | 3.4 | 4.5 | 3.6 | 2.3 | 2.5 | 1.5 |
| YVAD-ald | >10,000 | >10,000 | >10,000 | >10,000 | >10,000 | >10,000 |

To determine if the presence of membrane derived caspase activity is a general property of mammalian cells, the DEVD-amc cleavage activity in heavy membranes from two other cell sources was measured: mouse E 15 primary brain cortical cells and the mouse dopaminergic MN9D cell line (Choi et al., *Neurobiology* 89:8943–8947, 1992). Heavy membrane fractions were prepared using identical procedures to those used for the 697 cells and were activated with caspase-1. These fractions contained a membrane derived caspase activity with similar cleavage activities per mg protein as observed in 697 cells (data not shown) and that was blocked by caspase inhibitors with a similar potency to that observed with fractions derived from 697 cells or with recombinant caspase-3 (Table II). Accordingly, the existence of membrane-derived caspase activity is not specific to 697 cells, but appears to be a general phenomenon.

Example 15

Exogenous Cytochrome C and Membrane Derived Procaspase-3

Several recent reports have shown that the release of cytochrome c from mitochondria can cause the activation of cytoplasmic caspase-3 (Liu et al., *Cell* 86:147–157, 1996; Li et al., *Cell* 91:479–489, 1997). Other reports have demonstrated that cytochrome c is released from mitochondria following apoptotic insults and that Bcl-2 can inhibit that release (Kluck et al., *Science* 275:1132–1136, 1997; Yang et al., *Science* 275:1129–1132, 1997). Thus, it was possible that the difference observed between caspase activities in heavy membranes from Bcl-2- and neo-expressing cells simply reflected inhibition by Bcl-2 of cytochrome c release during preparation of the heavy membrane fractions or during subsequent incubation of these fractions. To investigate this possibility, cell fractionation was performed in the presence of exogenous cytochrome c and measured whether this influenced caspase activation. If the Bcl-2-membranes had low caspase activity because of a Bcl-2 effect on cytochrome c sequestration, then the addition of exogenous cytochrome c during membrane fractionation should increase the caspase activity derived from those membranes to the levels seen in membranes from neo-cells. Accordingly, during the fractionation procedure for heavy membranes from neo- and Bcl-2-expressing cells, following Dounce homogenization, the sample was split into two fractions. One fraction was processed with standard buffers, while to the other fraction 10 μg/ml of bovine cytochrome c was added, and 10 μg/ml to the buffers used to suspend and wash the heavy membranes. This concentration of cytochrome c was chosen since it represents the estimated total amount of cytochrome c present in the starting cell pellets (Li et al., *J. Biol. Chem.* 272:30299–30305, 1997). Finally, these membranes were resuspended in 1 μg/ml cytochrome c plus 50 μM dATP, incubated, and then assayed for DEVD-amc cleaving activity. Aliquots of the cytochrome c-treated heavy membranes and cytoplasmic fractions were then incubated with hypotonic buffer containing 50 μM dATP/1 μg/ml cytochrome c for 40 min at 30° C., while the membranes and cytoplasmic samples that had not been treated with cytochrome c were incubated only with buffer. Each sample was then centrifuged, and DEVD-amc cleavage activity in the supernatant was measured. The data in FIG. 12 represents three equivalent experiments. This activity was compared to that from our usual membrane preparations prepared without cytochrome c, and incubated without cytochrome c or dATP.

Figures 12A, 12B:
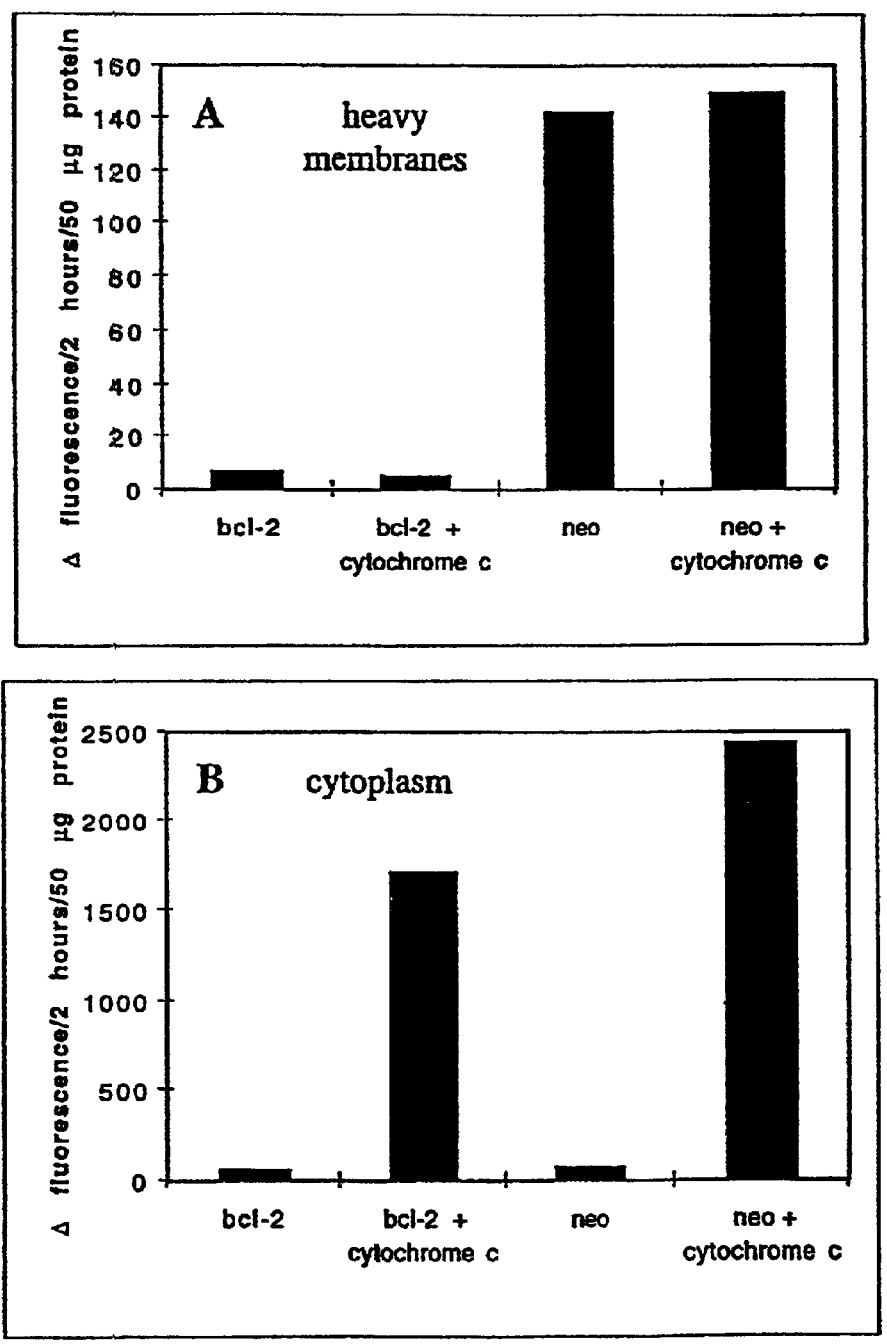
FIGS. 12A and 12B are graphical representations of DEVD-amc (SEQ ID NO:6) cleavage activity in 697-neo and 697-Bcl-2 cells in the presence and absence of cytochrome c.

The data demonstrate that inclusion of cytochrome c during membrane fractionation and incubation has no effect on membrane-derived caspase activity; the activity in the membranes derived from Bcl-2-expressing cells remained low compared to the activity in the neo-membranes, and furthermore, there was also no effect of cytochrome c on the caspase activity derived from the neo-membranes (FIG. 12A). Although the cytochrome c treatments did not activate the membrane derived caspase, the enzyme could still be activated by subsequent treatment with exogenous caspase-1 (data not shown). The lack of a cytochrome c effect on the activation of the membrane caspase was not due to an inactive preparation of cytochrome c, since the DEVD-amc cleavage activity of the cytoplasmic fractions from both neo and Bcl-2 cells were strongly activated by inclusion of cytochrome c during fractionation and assay (FIG. 12B). Therefore, Bcl-2 expression suppresses the activation of the membrane derived procaspase-3, but this effect is not overcome by addition of exogenous cytochrome c. Furthermore, Bcl-2 over-expression did not affect the ability of cytochrome c to activate caspase-3 in cytoplasmic fractions.

Example 16

Release of Membrane-Derived Caspase is Not Via Simple Leakage from Organelles A recent report described the presence of procaspase-3 in the intermembrane space within mitochondria (Mancini et al., *J. Cell Biol.* 140:1485–1495, 1998). Thus, it was possible that this material could account for the activatable caspase activity that was measured in the mitochondria-containing heavy membrane fractions. Furthermore, it was possible that the spontaneous activity that was measured in membrane fractions from 697-neo cells was due to leakage of active caspase from mitochondria, and that mitochondria isolated from 697-Bcl-2 cells were simply less leaky (Yang et al., *Science* 275:1129–1132, 1997). However, several experiments suggested that the activity measured was not due to leakage from mitochondria, and that the activity is distinct from that described by Mancini et al., supra.

Figure 13A:
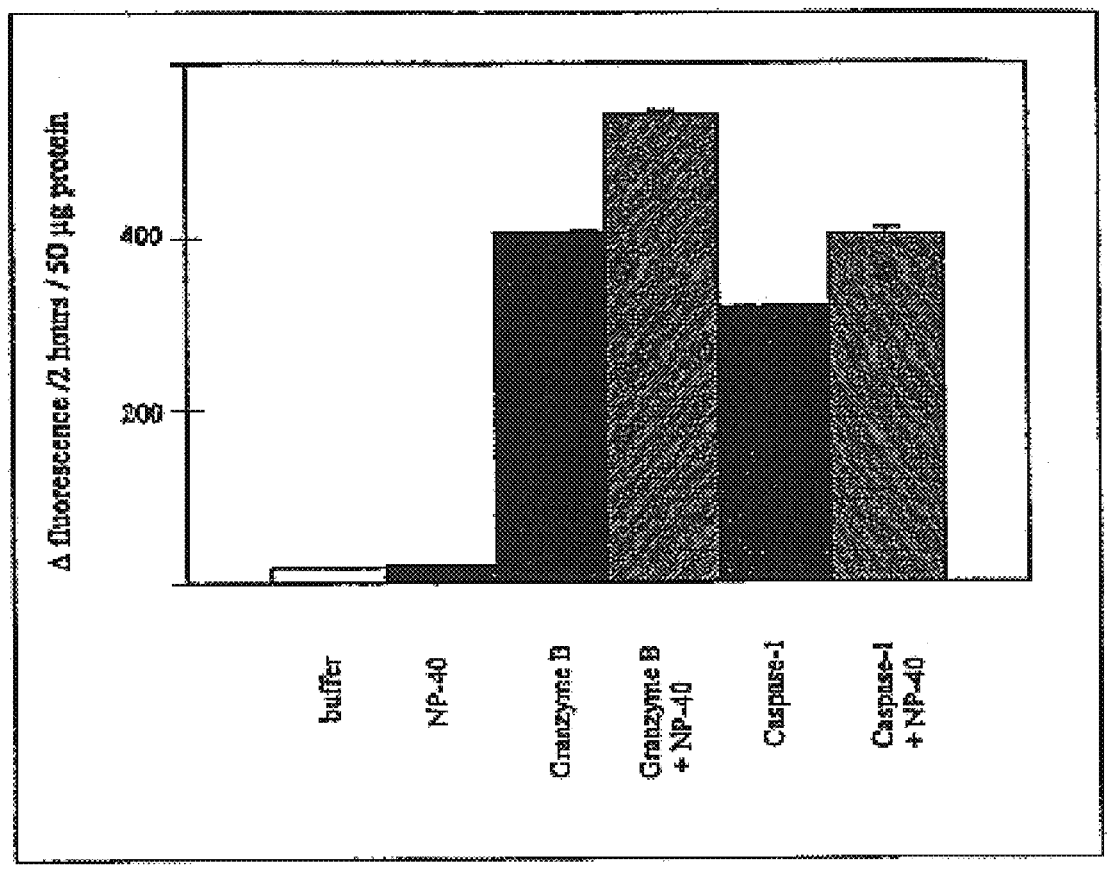
FIGS. 13A, 13B, and 13C are graphs representing the effects of permeabilizing detergents on membrane-associated caspase activity.
Figure 13B:
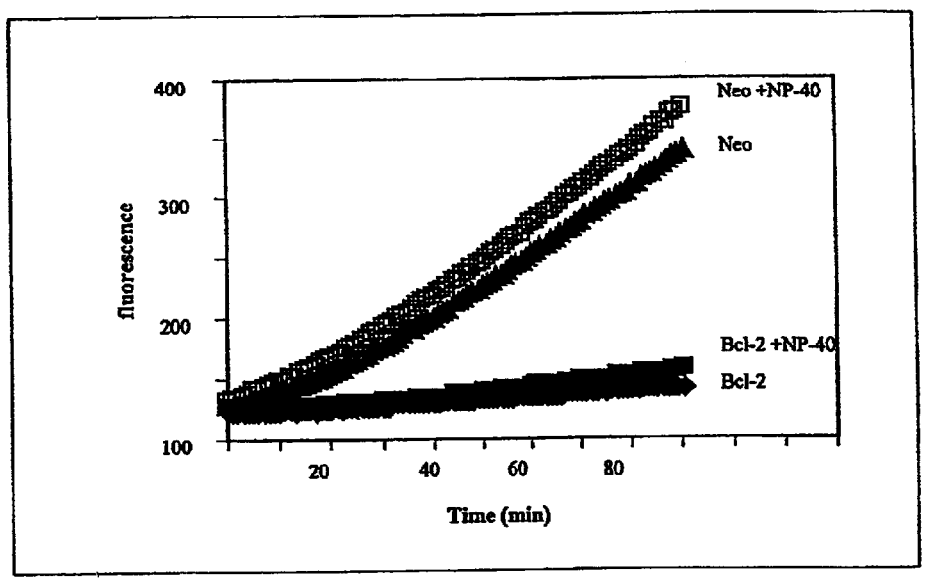

First, whether the addition of 1% NP-40 to neo-membranes affected the level of either spontaneous activity or the activity induced by caspase-1 or granzyme B was tested. It was reasoned that if procaspase and/or active caspase was sequestered within organelles, then enhanced activity would be measured in the presence of NP-40. Treatment with 1% NP-40 was sufficient to release almost all of the cytochrome c present in heavy membrane preparations (data not shown). Furthermore, it was shown by Mancini and colleagues that treatment of their mitochondrial preparations with 1% NP-40 allowed granzyme B to cleave procaspase-3 whereas no cleavage was observed in the absence of detergent (Mancini et al., *J. Cell Biol.* 140:1485–1495, 1998). However, the present results demonstrate that 1% NP-40 had little effect either on spontaneous activity or the activity induced by treatment with caspase-1 or granzyme B (FIG. 12A). In this experiment, 160 μl of neo-membranes were diluted with 180 μl hypotonic buffer and treated with 40 μl 10% NP-40 detergent or dH$_2$O (final vol=380 μl). The diluted membranes were activated by the addition of 20 μl granzyme B or caspase-1 lysate or buffer, and incubated for 60 min at 30° C. Following activation, the heavy membranes were removed by centrifugation and the DEVD-amc cleaving activity of each sample was measured by adding 50 μl of each supernatant to 200 μl of 25 μM DEVD-amc substrate in ICE buffer (FIG. 13A).

Next, to analyze whether membrane preparations from 697-Bcl-2 cells may have low spontaneous activity due to enhanced sequestration of a caspase, DEVD-amc was added to Bcl-2- and neo-membrane preparations, incubated them in buffer alone or buffer plus 1% NP-40, and measured the appearance of fluorescence. In this experiment, the effect of NP-40 on the progress curve for heavy membrane catalyzed DEVD-amc hydrolysis was measured by adding 50 μl freshly prepared neo-or Bcl-2-membranes to 200 μl 25 uM DEVD-amc in hypotonic buffer pH 7.5 (containing 4 mM DTT) with or without 1% NP-40 detergent. The results indicate that 1% NP-40 had only a minor effect on the magnitude or rate of fluorescence increase. Preparations derived from 697-Bcl-2 cells had low activity regardless of whether 1% NP-40 was present, demonstrating that this low level of activity was not due to sequestration of an active caspase.

Figure 13C:
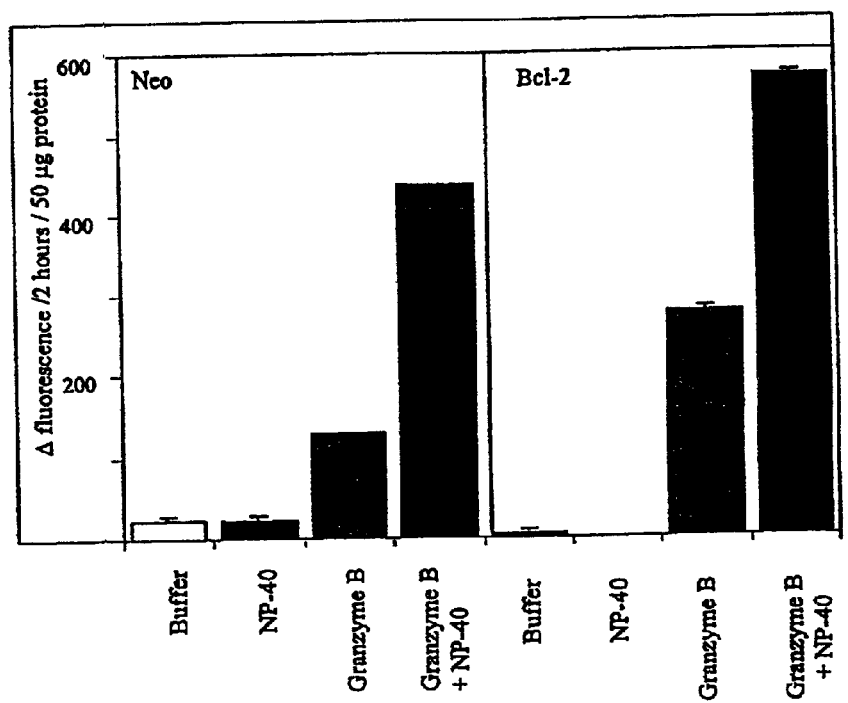

Lastly, mitochondrial fractions from 697-neo and 697-Bcl-2 cells were prepared using the methods described by Mancini et al (1998) to more directly assess the relationship between our results and their published data. In this experiment, diluted membranes, with or without 1% NP-40, were activated by the addition of granzyme B or buffer for 60 min, centrifuged, and assayed for DEVD-amc cleavage activity as described in FIG. 13A. As is shown in FIG. 13C, fractions from both 697-neo and 697-Bcl-2 made by these methods have granzyme B-activatable caspase activity in the absence of NP-40. However, in the presence of 1% NP-40, granzyme B treatment yielded enhanced caspase activity.

Thus, under these conditions, granzyme B generates caspase activity in both NP-40 independent and dependent manners.

Example 17

Characterization of Purified Membrane Derived Procaspase-3 Activity

Figure 6:
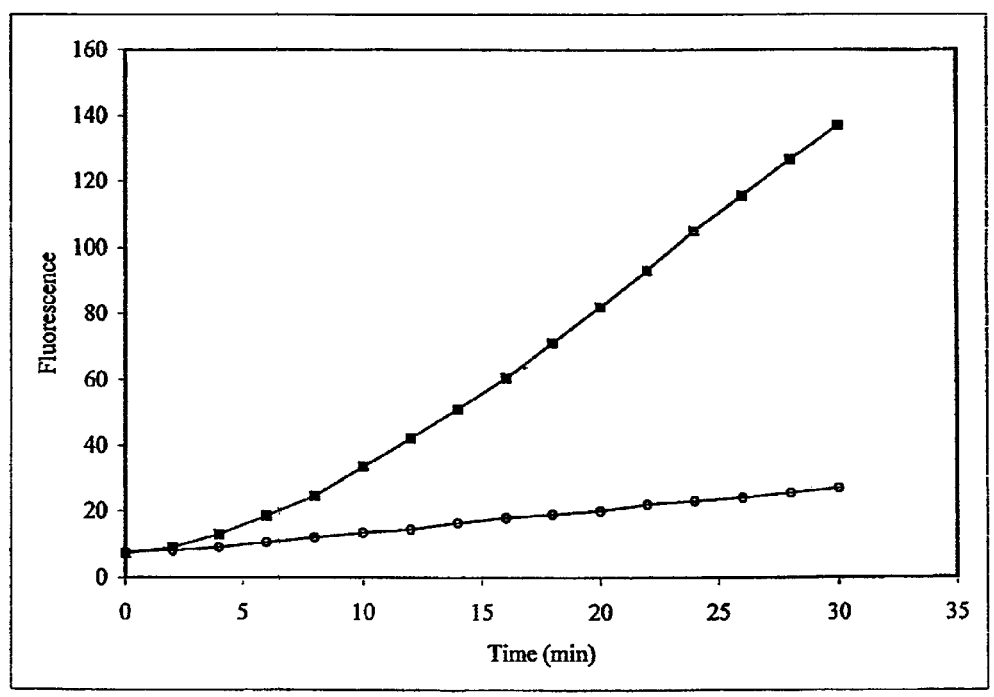
FIG. 6 is a graph illustrating the DEVD-amc (SEQ ID NO:6) hydrolysis activity of affinity purified membrane derived caspase-3 from 697 cell membranes wherein the enzyme is rapidly activated in the presence of DTT (squares), while little or no activation occurs in the absence of DTT (circles).

As noted in Example 7, the membrane derived caspase-3 was also eluted from an affinity column under nondenaturing conditions using hydroxylamine/glutathione. The oxidized caspase was rapidly reduced by 6 mM DTT to its active form, which efficiently cleaves the DEVD-AMC substrate (FIG. 6). The steady-state kinetic and inhibitory parameters of the reactivated membrane derived caspase-3 were measured in order to compare the membrane derived caspase-3 to previously isolated forms of caspase-3 from other sources. The observed $K_M$ value for the purified caspase (10 μM) is essentially identical to the $K_M$ value for bacterially expressed $Ni^{+2}$-purified recombinant caspase-3 as well as caspase-3 isolated from THP-1 cell cytoplasm.

The inhibition of DEVD-AMC cleavage activity by several caspase inhibitors were also measured (Table III). For each peptide aldehyde, the $IC_{50}$ values for the inhibition of membrane derived caspase-3 are very similar to those of recombinant caspase-3. The heavy membrane caspase from 697 cells is also potently inhibited by recombinant baculovirus p35 protein ($IC_{50}$=74 pM). Using this $IC_{50}$ to set an upper limit on the enzyme concentration, the $k_{cat}/K_M$ for DEVD-AMC hydrolysis must be ≧400,000 $M^{-1}sec^{-1}$, which is close to the $k_{cat}/K_M$ value for the recombinant caspase-3 (1,200,000 $M^{-1}sec^{-1}$). Collectively our data indicate that affinity purified membrane derived caspase-3 and $Ni^{+2}$-purified recombinant caspase-3 are functionally indistinguishable.

TABLE III

Comparison of Caspase Inhibitor $IC_{50}$ Values of Purified Membrane Derived and Recombinant Caspase-3 Polypeptides.

| | $IC_{50}$ (nM) | |
|---|---|---|
| Inhibitor | Membrane | Recombinant |
| DEVDald | 1.0 | 1.0 |
| ZEVDald | 32 | 24 |
| DFLDald | 4.7 | 1.1 |
| VEIDald | 34 | 32 |
| Baculovirus p35 | 0.074 | 0.041 |

From the foregoing it will be appreciated that, although specific embodiments of the invention have been described herein for purposes of illustration, various modifications may be made without deviating from the spirit and scope of the invention. Accordingly, the invention is not limited except as by the appended claims. Further, all patents, patent applications, articles, and various other references are hereby incorporated by reference in their entirety.

What is claimed is:

1. An isolated nucleic acid molecule comprising a sequence encoding a membrane derived caspase-3 polypeptide of SEQ ID NO:3, wherein said nucleic acid molecule does not comprise a sequence encoding cytoplasmic procaspase-3 polypeptide of SEQ ID NO:1 encoded by a sequence encoding a cytoplasmic caspase-3 polypeptide corresponding to amino acid residues encoded by nucleotides 30–834 of SEQ ID NO:1.

2. The nucleic acid molecule of claim 1 wherein the membrane derived caspase-3 oligomerizes with a caspase.

3. An isolated nucleic acid molecule encoding a membrane derived caspase-3 comprising a single stranded or double stranded polynucleotide sequence of SEQ ID NO:2, wherein said nucleic acid molecule does not comprise a sequence encoding the cytoplasmic procaspase-3 polypeptide encoding by SEQ ID NO:1 or a sequence encoding a cytoplasmic caspase-3 polypeptide corresponding to amino acid residues encoded by nucleotides 30–834.

4. A vector, comprising the nucleic acid molecule of any one of claims 1 or 3.

5. The vector of claim 4 wherein the vector is a viral vector.

6. A nucleic acid expression vector, comprising the nucleic acid molecule of any one of claims 1–3 wherein the nucleic acid molecule is operably linked to a promoter.

7. The vector of claim 6 wherein the promoter is an inducible promoter.

8. A host cell containing the vector of claim 6.

9. A host cell containing the vector of claim 7.

10. The host cell of claim 8 wherein the host cell is selected from the group consisting of a bacterium, a yeast cell, a nematode cell, an insect cell, and a mammalian cell.

11. The host cell of claim 9 wherein the host cell is selected from the group consisting of a bacterium, a yeast cell, a nematode cell, an insect cell, and a mammalian cell.

12. A method of producing a membrane derived caspase-3 polypeptide, comprising culturing a host cell containing a nucleic acid expression vector comprising at least one promoter operably linked to a nucleic acid molecule encoding a membrane derived caspase-3 polypeptide, the nucleic acid molecule comprising SEQ ID NO:2, under conditions and for a time sufficient for expression of the polypeptide, wherein said nucleic acid molecule does not comprise a sequence encoding the cytoplasmic procaspase-3 polypeptide encoded by SEQ ID NO:1 or a sequence encoding a cytoplasmic caspase-3 polypeptide corresponding to amino acid residues encoded by nucleotides 30–834 of SEQ ID NO:1.

13. The method of claim 12 wherein the promoter is inducible.

14. The method of any one of claims 12–13, further comprising contacting the host cell with a caspase activator under conditions and for a time sufficient to activate the membrane derived caspase-3 polypeptide.

15. A gene delivery vehicle comprising a nucleic acid molecule according to any one of claims 1–3 wherein the nucleic acid molecule is operably linked to a promoter.

16. The gene delivery vehicle of claim 15 wherein the vehicle is a retrovirus or adenovirus.

17. The gene delivery vehicle of claim 15 wherein the nucleic acid molecule is associated with a polycation.

18. The gene delivery vehicle of claim 15, further comprising a ligand that binds a cell surface receptor.

19. A kit for screening for agents that alter apoptosis, comprising a host cell and an isolated nucleic acid molecule comprising a sequence encoding a membrane derived caspase-3 polypeptide of SEQ ID NO:3, wherein said nucleic acid molecule does not comprise a sequence encoding the cytoplasmic procaspase-3 polypeptide encoded by SEQ ID NO:1 or a sequence encoding a cytoplasmic caspase-3 polypeptide corresponding to amino acid residues encoded by nucleotides 30–834.

20. The kit according to claim 19 wherein the host cell is a eukaryotic cell.

21. The kit according to claim 20 wherein the host cell is selected from the group consisting of 697 lymphoblastoid cells, E15 primary brain cortical cells, MN9D cells, Jurkat T cells, THP-1 cells, and FL5. 12 cells.

* * * * *

SEQUENCE LISTING

<160> NUMBER OF SEQ ID NOS: 7

<210> SEQ ID NO 1
<211> LENGTH: 834
<212> TYPE: DNA

<213> ORGANISM: Homo sapien
<220> FEATURE:
<221> NAME/KEY: CDS
<222> LOCATION: (1)...(834)

<400> SEQUENCE: 1

```
atg gag aac act gaa aac tca gtg gat tca aaa tcc att aaa aat ttg        48
Met Glu Asn Thr Glu Asn Ser Val Asp Ser Lys Ser Ile Lys Asn Leu
1               5                   10                  15 gaa cca aag atc ata cat gga agc gaa tca atg gac tct gga ata tcc        96
Glu Pro Lys Ile Ile His Gly Ser Glu Ser Met Asp Ser Gly Ile Ser
            20                  25                  30 ctg gac aac agt tat aaa atg gat tat cct gag atg ggt tta tgt ata       144
Leu Asp Asn Ser Tyr Lys Met Asp Tyr Pro Glu Met Gly Leu Cys Ile
        35                  40                  45 ata att aat aat aag aat ttt cat aaa agc act gga atg aca tct cgg       192
Ile Ile Asn Asn Lys Asn Phe His Lys Ser Thr Gly Met Thr Ser Arg
    50                  55                  60 tct ggt aca gat gtc gat gca gca aac ctc agg gaa aca ttc aga aac       240
Ser Gly Thr Asp Val Asp Ala Ala Asn Leu Arg Glu Thr Phe Arg Asn
65                  70                  75                  80 ttg aaa tat gaa gtc agg aat aaa aat gat ctt aca cgt gaa gaa att       288
Leu Lys Tyr Glu Val Arg Asn Lys Asn Asp Leu Thr Arg Glu Glu Ile
                85                  90                  95 gtg gaa ttg atg cgt gat gtt tct aaa gaa gat cac agc aaa agg agc       336
Val Glu Leu Met Arg Asp Val Ser Lys Glu Asp His Ser Lys Arg Ser
            100                 105                 110 agt ttt gtt tgt gtg ctt ctg agc cat ggt gaa gaa gga ata att ttt       384
Ser Phe Val Cys Val Leu Leu Ser His Gly Glu Glu Gly Ile Ile Phe
        115                 120                 125 gga aca aat gga cct gtt gac ctg aaa aaa ata aca aac ttt ttc aga       432
Gly Thr Asn Gly Pro Val Asp Leu Lys Lys Ile Thr Asn Phe Phe Arg
    130                 135                 140 ggg gat cgt tgt aga agt cta act gga aaa ccc aaa ctt ttc att att       480
Gly Asp Arg Cys Arg Ser Leu Thr Gly Lys Pro Lys Leu Phe Ile Ile
145                 150                 155                 160 cag gcc tgc cgt ggt aca gaa ctg gac tgt ggc att gag aca gac agt       528
Gln Ala Cys Arg Gly Thr Glu Leu Asp Cys Gly Ile Glu Thr Asp Ser
                165                 170                 175 ggt gtt gat gat gac atg gcg tgt cat aaa ata cca gtg gat gcc gac       576
Gly Val Asp Asp Asp Met Ala Cys His Lys Ile Pro Val Asp Ala Asp
            180                 185                 190 ttc ttg tat gca tac tcc aca gca cct ggt tat tat tct tgg cga aat       624
Phe Leu Tyr Ala Tyr Ser Thr Ala Pro Gly Tyr Tyr Ser Trp Arg Asn
        195                 200                 205 tca aag gat ggc tcc tgg ttc atc cag tcg ctt tgt gcc atg ctg aaa       672
Ser Lys Asp Gly Ser Trp Phe Ile Gln Ser Leu Cys Ala Met Leu Lys
    210                 215                 220 cag tat gcc gac aag ctt gaa ttt atg cac att ctt acc cgg gtt aac       720
Gln Tyr Ala Asp Lys Leu Glu Phe Met His Ile Leu Thr Arg Val Asn
225                 230                 235                 240 cga aag gtg gca aca gaa ttt gag tcc ttt tcc ttt gac gct act ttt       768
Arg Lys Val Ala Thr Glu Phe Glu Ser Phe Ser Phe Asp Ala Thr Phe
                245                 250                 255 cat gca aag aaa cag att cca tgt att gtt tcc atg ctc aca aaa gaa       816
His Ala Lys Lys Gln Ile Pro Cys Ile Val Ser Met Leu Thr Lys Glu
            260                 265                 270 ctc tat ttt tat cac taa                                               834
Leu Tyr Phe Tyr His *
        275
```

<210> SEQ ID NO 2
<211> LENGTH: 795
<212> TYPE: DNA
<213> ORGANISM: Homo sapien
<220> FEATURE:
<221> NAME/KEY: CDS
<222> LOCATION: (1)...(795)

<400> SEQUENCE: 2

| | | | | | | | | | | | | | | | | |
|---|---|---|---|---|---|---|---|---|---|---|---|---|---|---|---|---|
| aaa | aat | ttg | gaa | cca | aag | atc | ata | cat | gga | agc | gaa | tca | atg | gac | tct | 48 |
| Lys | Asn | Leu | Glu | Pro | Lys | Ile | Ile | His | Gly | Ser | Glu | Ser | Met | Asp | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gga | ata | tcc | ctg | gac | aac | agt | tat | aaa | atg | gat | tat | cct | gag | atg | ggt | 96 |
| Gly | Ile | Ser | Leu | Asp | Asn | Ser | Tyr | Lys | Met | Asp | Tyr | Pro | Glu | Met | Gly | |
| | | | 20 | | | | | 25 | | | | | 30 | | | |

| | | | | | | | | | | | | | | | | |
|---|---|---|---|---|---|---|---|---|---|---|---|---|---|---|---|---|
| tta | tgt | ata | ata | att | aat | aat | aag | aat | ttt | cat | aaa | agc | act | gga | atg | 144 |
| Leu | Cys | Ile | Ile | Ile | Asn | Asn | Lys | Asn | Phe | His | Lys | Ser | Thr | Gly | Met | |
| | | 35 | | | | | 40 | | | | | 45 | | | | |

| | | | | | | | | | | | | | | | | |
|---|---|---|---|---|---|---|---|---|---|---|---|---|---|---|---|---|
| aca | tct | cgg | tct | ggt | aca | gat | gtc | gat | gca | gca | aac | ctc | agg | gaa | aca | 192 |
| Thr | Ser | Arg | Ser | Gly | Thr | Asp | Val | Asp | Ala | Ala | Asn | Leu | Arg | Glu | Thr | |
| 50 | | | | | 55 | | | | | 60 | | | | | | |

| | | | | | | | | | | | | | | | | |
|---|---|---|---|---|---|---|---|---|---|---|---|---|---|---|---|---|
| ttc | aga | aac | ttg | aaa | tat | gaa | gtc | agg | aat | aaa | aat | gat | ctt | aca | cgt | 240 |
| Phe | Arg | Asn | Leu | Lys | Tyr | Glu | Val | Arg | Asn | Lys | Asn | Asp | Leu | Thr | Arg | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gaa | gaa | att | gtg | gaa | ttg | atg | cgt | gat | gtt | tct | aaa | gaa | gat | cac | agc | 288 |
| Glu | Glu | Ile | Val | Glu | Leu | Met | Arg | Asp | Val | Ser | Lys | Glu | Asp | His | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| aaa | agg | agc | agt | ttt | gtt | tgt | gtg | ctt | ctg | agc | cat | ggt | gaa | gaa | gga | 336 |
| Lys | Arg | Ser | Ser | Phe | Val | Cys | Val | Leu | Leu | Ser | His | Gly | Glu | Glu | Gly | |
| | | | 100 | | | | | 105 | | | | | 110 | | | |

| | | | | | | | | | | | | | | | | |
|---|---|---|---|---|---|---|---|---|---|---|---|---|---|---|---|---|
| ata | att | ttt | gga | aca | aat | gga | cct | gtt | gac | ctg | aaa | aaa | ata | aca | aac | 384 |
| Ile | Ile | Phe | Gly | Thr | Asn | Gly | Pro | Val | Asp | Leu | Lys | Lys | Ile | Thr | Asn | |
| | | 115 | | | | | 120 | | | | | 125 | | | | |

| | | | | | | | | | | | | | | | | |
|---|---|---|---|---|---|---|---|---|---|---|---|---|---|---|---|---|
| ttt | ttc | aga | ggg | gat | cgt | tgt | aga | agt | cta | act | gga | aaa | ccc | aaa | ctt | 432 |
| Phe | Phe | Arg | Gly | Asp | Arg | Cys | Arg | Ser | Leu | Thr | Gly | Lys | Pro | Lys | Leu | |
| 130 | | | | | 135 | | | | | 140 | | | | | | |

| | | | | | | | | | | | | | | | | |
|---|---|---|---|---|---|---|---|---|---|---|---|---|---|---|---|---|
| ttc | att | att | cag | gcc | tgc | cgt | ggt | aca | gaa | ctg | gac | tgt | ggc | att | gag | 480 |
| Phe | Ile | Ile | Gln | Ala | Cys | Arg | Gly | Thr | Glu | Leu | Asp | Cys | Gly | Ile | Glu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| aca | gac | agt | ggt | gtt | gat | gat | gac | atg | gcg | tgt | cat | aaa | ata | cca | gtg | 528 |
| Thr | Asp | Ser | Gly | Val | Asp | Asp | Asp | Met | Ala | Cys | His | Lys | Ile | Pro | Val | |
| | | | 165 | | | | | 170 | | | | | 175 | | | |

| | | | | | | | | | | | | | | | | |
|---|---|---|---|---|---|---|---|---|---|---|---|---|---|---|---|---|
| gat | gcc | gac | ttc | ttg | tat | gca | tac | tcc | aca | gca | cct | ggt | tat | tat | tct | 576 |
| Asp | Ala | Asp | Phe | Leu | Tyr | Ala | Tyr | Ser | Thr | Ala | Pro | Gly | Tyr | Tyr | Ser | |
| | | 180 | | | | | 185 | | | | | 190 | | | | |

| | | | | | | | | | | | | | | | | |
|---|---|---|---|---|---|---|---|---|---|---|---|---|---|---|---|---|
| tgg | cga | aat | tca | aag | gat | ggc | tcc | tgg | ttc | atc | cag | tcg | ctt | tgt | gcc | 624 |
| Trp | Arg | Asn | Ser | Lys | Asp | Gly | Ser | Trp | Phe | Ile | Gln | Ser | Leu | Cys | Ala | |
| | | | 195 | | | | | 200 | | | | | 205 | | | |

| | | | | | | | | | | | | | | | | |
|---|---|---|---|---|---|---|---|---|---|---|---|---|---|---|---|---|
| atg | ctg | aaa | cag | tat | gcc | gac | aag | ctt | gaa | ttt | atg | cac | att | ctt | acc | 672 |
| Met | Leu | Lys | Gln | Tyr | Ala | Asp | Lys | Leu | Glu | Phe | Met | His | Ile | Leu | Thr | |
| | | 210 | | | | | 215 | | | | | 220 | | | | |

| | | | | | | | | | | | | | | | | |
|---|---|---|---|---|---|---|---|---|---|---|---|---|---|---|---|---|
| cgg | gtt | aac | cga | aag | gtg | gca | aca | gaa | ttt | gag | tcc | ttt | tcc | ttt | gac | 720 |
| Arg | Val | Asn | Arg | Lys | Val | Ala | Thr | Glu | Phe | Glu | Ser | Phe | Ser | Phe | Asp | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gct | act | ttt | cat | gca | aag | aaa | cag | att | cca | tgt | att | gtt | tcc | atg | ctc | 768 |
| Ala | Thr | Phe | His | Ala | Lys | Lys | Gln | Ile | Pro | Cys | Ile | Val | Ser | Met | Leu | |
| | | | 245 | | | | | 250 | | | | | 255 | | | |

| | | | | | | | |
|---|---|---|---|---|---|---|---|
| aca | aaa | gaa | ctc | tat | ttt | tat | cac | taa | 795 |
| Thr | Lys | Glu | Leu | Tyr | Phe | Tyr | His | * | |
| | | | 260 | | | | | | |

-continued

```
<210> SEQ ID NO 3
<211> LENGTH: 264
<212> TYPE: PRT
<213> ORGANISM: Homo sapien

<400> SEQUENCE: 3

Lys Asn Leu Glu Pro Lys Ile Ile His Gly Ser Glu Ser Met Asp Ser
 1               5                  10                  15

Gly Ile Ser Leu Asp Asn Ser Tyr Lys Met Asp Tyr Pro Glu Met Gly
            20                  25                  30

Leu Cys Ile Ile Ile Asn Asn Lys Asn Phe His Lys Ser Thr Gly Met
        35                  40                  45

Thr Ser Arg Ser Gly Thr Asp Val Asp Ala Ala Asn Leu Arg Glu Thr
    50                  55                  60

Phe Arg Asn Leu Lys Tyr Glu Val Arg Asn Lys Asn Asp Leu Thr Arg
65                  70                  75                  80

Glu Glu Ile Val Glu Leu Met Arg Asp Val Ser Lys Glu Asp His Ser
                85                  90                  95

Lys Arg Ser Ser Phe Val Cys Val Leu Leu Ser His Gly Glu Glu Gly
            100                 105                 110

Ile Ile Phe Gly Thr Asn Gly Pro Val Asp Leu Lys Lys Ile Thr Asn
        115                 120                 125

Phe Phe Arg Gly Asp Arg Cys Arg Ser Leu Thr Gly Lys Pro Lys Leu
    130                 135                 140

Phe Ile Ile Gln Ala Cys Arg Gly Thr Glu Leu Asp Cys Gly Ile Glu
145                 150                 155                 160

Thr Asp Ser Gly Val Asp Asp Met Ala Cys His Lys Ile Pro Val
                165                 170                 175

Asp Ala Asp Phe Leu Tyr Ala Tyr Ser Thr Ala Pro Gly Tyr Tyr Ser
            180                 185                 190

Trp Arg Asn Ser Lys Asp Gly Ser Trp Phe Ile Gln Ser Leu Cys Ala
        195                 200                 205

Met Leu Lys Gln Tyr Ala Asp Lys Leu Glu Phe Met His Ile Leu Thr
    210                 215                 220

Arg Val Asn Arg Lys Val Ala Thr Glu Phe Glu Ser Phe Ser Phe Asp
225                 230                 235                 240

Ala Thr Phe His Ala Lys Lys Gln Ile Pro Cys Ile Val Ser Met Leu
                245                 250                 255

Thr Lys Glu Leu Tyr Phe Tyr His
            260

<210> SEQ ID NO 4
<211> LENGTH: 30
<212> TYPE: PRT
<213> ORGANISM: Homo sapien

<400> SEQUENCE: 4

Met Glu Asn Thr Glu Asn Ser Val Asp Ser Lys Ser Ile Lys Asn Leu
 1               5                  10                  15

Glu Pro Lys Ile Ile His Gly Ser Glu Ser Met Asp Ser Gly
            20                  25                  30

<210> SEQ ID NO 5
<211> LENGTH: 5
<212> TYPE: PRT
<213> ORGANISM: Homo sapien
```

-continued

```
<400> SEQUENCE: 5

Gln Ala Cys Arg Gly
 1               5

<210> SEQ ID NO 6
<211> LENGTH: 4
<212> TYPE: PRT
<213> ORGANISM: Homo sapien

<400> SEQUENCE: 6

Asp Glu Val Asp
 1

<210> SEQ ID NO 7
<211> LENGTH: 4
<212> TYPE: PRT
<213> ORGANISM: Homo sapien

<400> SEQUENCE: 7

Tyr Val Ala Asp
 1
```